United States Patent
Wang

(10) Patent No.: US 10,927,077 B2
(45) Date of Patent: Feb. 23, 2021

(54) PROCESS FOR PREPARING INTERMEDIATE OF ANTI-TUMOR DRUG NIRAPARIB AND INTERMEDIATE THEREOF

(71) Applicant: ZAI LAB (SHANGHAI) CO., LTD., Shanghai (CN)

(72) Inventor: Tianhao Wang, Shanghai (CN)

(73) Assignee: ZAI LAB (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/755,561

(22) PCT Filed: Oct. 12, 2018

(86) PCT No.: PCT/CN2018/110025
§ 371 (c)(1),
(2) Date: Apr. 10, 2020

(87) PCT Pub. No.: WO2019/072237
PCT Pub. Date: Apr. 18, 2019

(65) Prior Publication Data
US 2020/0385350 A1    Dec. 10, 2020

(30) Foreign Application Priority Data
Oct. 13, 2017   (CN) .......................... 201710953949.7

(51) Int. Cl.
C07D 211/02   (2006.01)
C07D 211/76   (2006.01)

(52) U.S. Cl.
CPC .......... *C07D 211/02* (2013.01); *C07D 211/76* (2013.01)

(58) Field of Classification Search
CPC .............................. C07D 211/02; C07D 211/76
See application file for complete search history.

(56) References Cited

U.S. PATENT DOCUMENTS

2004/0171836 A1   9/2004   Fujino

FOREIGN PATENT DOCUMENTS

| CN | 106432056 A | 2/2017 |
|----|-------------|--------|
| CN | 106432057 A | 2/2017 |
| CN | 106432058 A | 2/2017 |
| CN | 106749180 A | 5/2017 |
| CN | 106749181 A | 5/2017 |
| CN | 106854176 A | 6/2017 |
| CN | 106883166 A | 6/2017 |
| CN | 109265390 A | 1/2019 |
| JP | H0413659 A  | 1/1992 |
| JP | H0474165 A  | 3/1992 |

OTHER PUBLICATIONS

European search report issued in the counterpart European application No. 188672257 dated Jul. 31, 2020.
1st Office Action issued in the counterpart European application No. 188672257 dated Aug. 27, 2020.
Notice of Grounds for Rejection issued in the counterpart Korean application No. 10-2020-7013496 dated Sep. 2, 2020.
Philipp Schafer Asymmetric Suzuki-Miyaura coupling of heterocycles via Rhodium-catalysed allylic arylation of racemates, Nature Communications, vol. 8, No. 1, Jun. 13, 2017.
International Search Report issued in International Patent Application No. PCT/CN2018/110025 dated Nov. 13, 2018.
Written Opinion of the International Searching Authority issued in International Patent Application No. PCT/CN2018/110025 dated Nov. 13, 2018.
Chinese Office Action issued in Chinese Patent Application No. 201811189194 dated Sep. 25, 2019.
Amat, Mercedes, et al., "Dynamic Kinetic Resolution of Racemic γ-Aryl-δ-oxoesters. Enantioselective Synthesis of 3-Arylpiperidines" J. Org. Chem., 67, 26, pp. 5343-5351, especially p. 5344, SCHEME 1, Jun. 2002 (Jun. 26, 2002).
Wallace, Debra J., et al., "Development of a Fit-for-Purpose Large-Scale Synthesis of an Oral PARP Inhibitor", Organic Process Research & Development, (2011) 15, American Chemical Society, pp. 831-840.
Chung, Cheol K., et al., "Process Development of C—N Cross-Coupling and Enantioselective Biocatalytic Reactions for the Asymmetric Synthesis of Niraparib", Organic Process Research & Development (2014) 18, pp. 215-227.

(Continued)

*Primary Examiner* — Timothy R Rozof
(74) *Attorney, Agent, or Firm* — Foley & Lardner LLP

(57) ABSTRACT

Disclosed is a process for preparing an intermediate of anti-tumor drug niraparib and an intermediate thereof. The present invention discloses a process for preparing compound f, which comprises conducting a cyclization reaction of compound e in a solvent and in the presence of a base to give compound f. The process of the present invention does not involve the steps of catalytic reduction or catalytic coupling reaction of precious metals and chiral separation, which has advantages such as low equipment requirements, simple operation, favorable industrial production, avoiding waste liquid containing heavy metals and phosphorus, low cost and high product ee value.

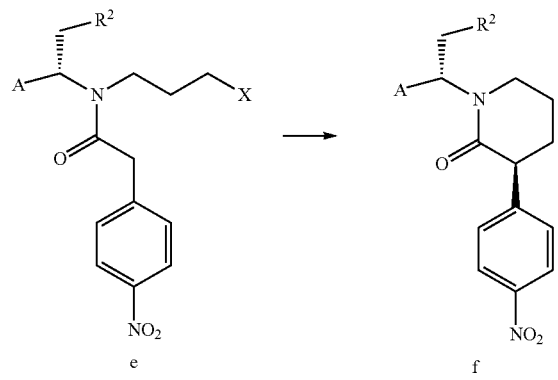

20 Claims, 1 Drawing Sheet

(56) References Cited

OTHER PUBLICATIONS

Davies, Stephen G., et al., "Asymmetric Syntheses of the Homalium Alkaloids (−)-(S,S)-Homaline and (−)-(R,R)-Hopromine", The Journal of Organic Chemistry (2012) 77(16), pp. 7028-7045.
Examination Report dated Nov. 2, 2020 issued in counterpart Indian application No. 202047018936, five (5) pages.

PROCESS FOR PREPARING INTERMEDIATE OF ANTI-TUMOR DRUG NIRAPARIB AND INTERMEDIATE THEREOF

The present application is the U.S. National Stage Entry of PCT International Application No. PCT/CN2018/110025, filed Oct. 12, 2018, which claims the benefit of Chinese Patent Application No. CN201710953949.7 filed on Oct. 13, 2017, the content of which is incorporated herein by reference in its entirety.

FIELD OF INVENTION

The present invention relates to a process for preparing an intermediate of anti-tumor drug niraparib and an intermediate thereof. Specifically, the present invention relates to a process for preparing (S)-4-(piperidin-3-yl)aniline and tert-butyl (S)-3-(4-aminophenyl)piperidin-1-carboxylate as intermediates of anti-tumor drug niraparib and intermediates thereof.

PRIOR ARTS

Niraparib (CAS: 1038915-60-4) is a novel PARP inhibitor developed by Tesaro, which is mainly used in the treatment of the cancer caused by BRCA1/2 mutations such as ovarian cancer and breast cancer. Niraparib was approved by FDA in March 2017 for the maintenance therapy in adult patients with epithelial ovarian cancer, fallopian tube cancer, or primary peritoneal cancer who have a complete or partial response but have relapsed after platinum-based chemotherapy (the growth of tumor is delayed). Clinical study showed that it could extend the median progression-free survival of patients by 280% to 22 months. Therefore, the drug has a promising potential for treating cancers.

Niraparib is named as 2-[4-((3S)-3-piperidinyl)phenyl]-2H-indazol-7-carboxamide represented by formula (I).

Formula (I)

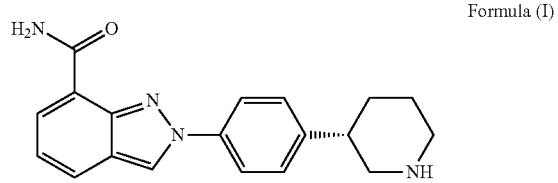 [SMILES: NC(=O)c1cccc2cn(-c3ccc([C@@H]4CCCNC4)cc3)nc12]

At present, several synthetic routes for preparing niraparib have been disclosed, wherein tert-butyl (S)-3-(4-aminophenyl)piperidin-1-carboxylate represented by formula (II) acts as an important intermediate.

Formula (II)

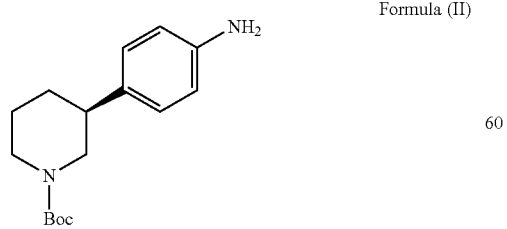

The reference (*Organic Process Research & Development* 2011, 15, 831-840) discloses a process for preparing tert-butyl (S)-3-(4-aminophenyl)piperidin-1-carboxylate as shown below, which comprises the following steps. Firstly, conducting a coupling reaction of 3-pyridineboronic acid and 4-nitrobromobenzene to give 3-(4-nitrophenyl)pyridine which is reduced by platinum oxide to give 4-(piperidin-3-yl)aniline. Then conducting a reaction of 4-(piperidin-3-yl)aniline and Boc$_2$O to give tert-butyl 3-(4-aminophenyl)piperidin-1-carboxylate, which is separated by chiral separation with L-dibenzoyltartaric acid as the resolving agent and methanol as the solvent to give tert-butyl (S)-3-(4-aminophenyl)piperidin-1-carboxylate.

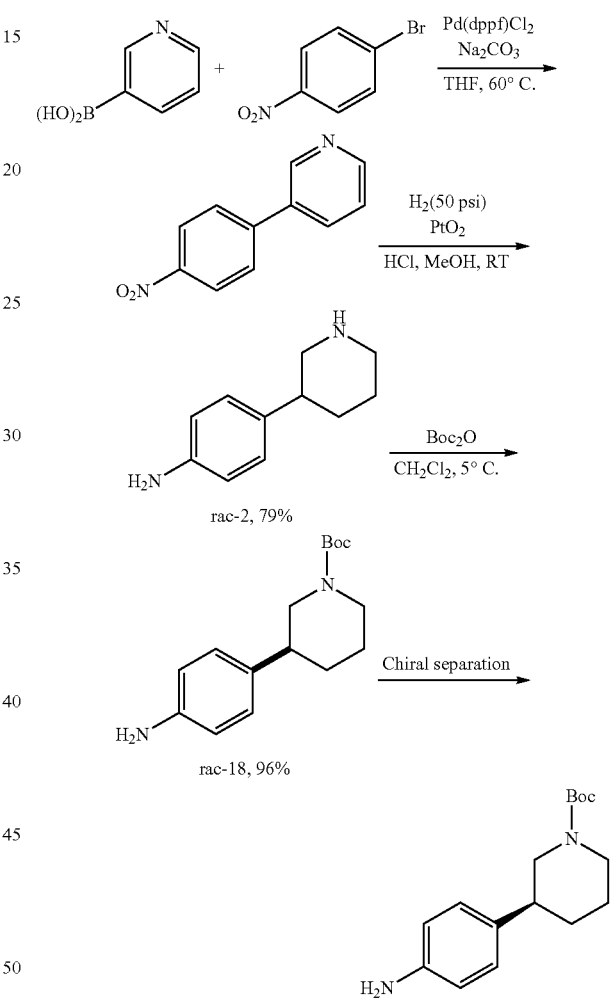

The reference (*Organic Process Research & Development* 2014, 18, 215-227) discloses a process for preparing tert-butyl (S)-3-(4-aminophenyl)piperidin-1-carboxylate as shown below, which comprises the following steps. Firstly, conducting a reduction reaction of 3-(4-nitrophenyl)pyridine in the presence of platinum oxide to give 4-(piperidin-3-yl)aniline. Then conducting a reaction of 4-(piperidin-3-yl)aniline and Boc$_2$O to give tert-butyl 3-(4-aminophenyl)piperidin-1-carboxylate, which is separated by chiral HPLC to give tert-butyl (S)-3-(4-aminophenyl)piperidin-1-carboxylate.

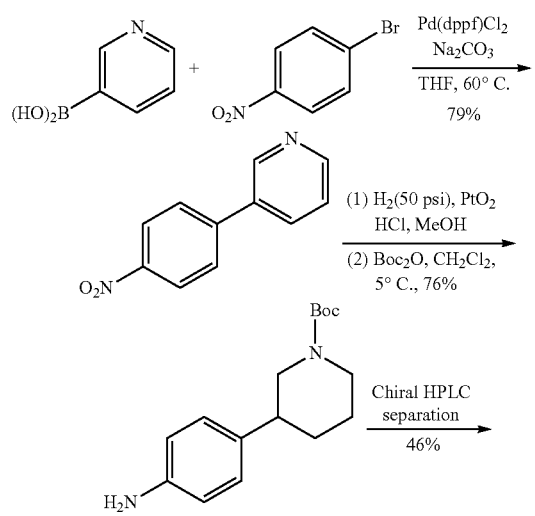

CN106432056A discloses a process for preparing tert-butyl (S)-3-(4-aminophenyl)piperidin-1-carboxylate comprising the following steps. Firstly, racemic tert-butyl 3-(4-aminophenyl)piperidin-1-carboxylate is separated with D-phenylglycine derivative as the resolving agent to give a salt of tert-butyl (S)-3-(4-aminophenyl)piperidin-1-carboxylate, which is hydrolyzed to give tert-butyl (S)-3-(4-aminophenyl)piperidin-1-carboxylate.

CN106432057A discloses a process for preparing tert-butyl (S)-3-(4-aminophenyl)piperidin-1-carboxylate, in which racemic tert-butyl 3-(4-aminophenyl)piperidin-1-carboxylate is separated by chiral separation with (R)-(−)-1,1'-binaphthyl-2,2'-diyl hydrogen phosphate as the resolving agent to give tert-butyl(S)-3-(4-aminophenyl)piperidin-1-carboxylate.

The processes for preparing (S)-4-(piperidin-3-yl)aniline and tert-butyl (S)-3-(4-aminophenyl)piperidin-1-carboxylate in the prior art mostly involve the steps of catalytic reduction using previous metals and/or chiral separation, which have defects such as high equipment requirements, complicated operation, unfavorable industrial production, high cost, and low product ee value.

The process of the present invention does not involve the steps of catalytic reduction or catalytic coupling reaction of precious metals and chiral separation, which has advantages such as low equipment requirements, simple operation, favorable industrial production, avoiding waste liquid containing heavy metals and phosphorus, low cost and high product ee value.

Content of the Present Invention

The technical problem to be solved in the present invention is to overcome the defects of the existing processes for preparing (S)-4-(piperidin-3-yl)aniline and tert-butyl (S)-3-(4-aminophenyl)piperidin-1-carboxylate in the prior art involve the steps of catalytic reduction or catalytic coupling reaction of precious metals and chiral separation which have defects such as high equipment requirements, complicated operation, unfavorable industrial production, high cost, and low product ee value. The present invention provides a process for preparing an intermediate of anti-tumor drug niraparib and an intermediate thereof. The process of the present invention does not involve the steps of catalytic reduction or catalytic coupling reaction of precious metals and chiral separation, which has advantages such as low equipment requirements, simple operation, favorable industrial production, avoiding waste liquid containing heavy metals and phosphorus, low cost and high product ee value.

The present invention solves the above-mentioned technical problems through the following technical solutions.

The present invention provides a process for preparing compound f, which comprises conducting a cyclization reaction of compound e in a solvent and in the presence of a base to give compound f;

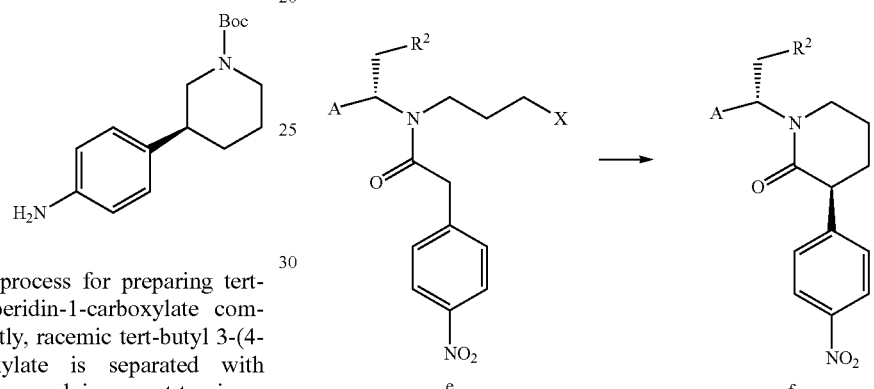

wherein, A is an aryl or a heteroaryl, each of which is optionally substituted by substituent(s) selected from the group consisting of H, D, an alkyl, hydroxy, an alkoxy, a halogen, an aryl, an aryloxy, an alkynyl, an alkenyl, a cycloalkyl, a cycloalkenyl, amino, an acyl, a heteroaryl, a heterocycloalkyl, an acylamido, nitro, cyano, mercapto or a haloalkyl; $R^2$ is H, an alkyl, hydroxy or an alkoxy; X is a leaving group, preferably a halogen (e.g. Cl, Br or I), methanesulfonyloxy (—$OSO_2CH_3$) or p-toluenesulfonyloxy (—OTs); wherein the number of the substituent(s) is 1 to 6, preferably 1 to 3. When the number of the substituents is 2, 3, 4, 5 or 6, the substituents can be the same or different.

In a preferred embodiment of the present invention, A is preferably

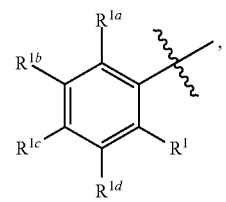

wherein each of $R^1$, $R^{1a}$, $R^{1b}$, $R^{1c}$ and $R^{1d}$ is independently H, D, the alkyl, hydroxy, an alkoxy, an halogen, an aryl, an aryloxy, an alkynyl, an alkenyl, a cycloalkyl, a cycloalkenyl, amino, an acylamido, a heteroaryl, a heterocycloalkyl, an acylamido, nitro, cyano, mercapto or a haloalkyl; $R^2$ is H, an alkyl, hydroxy or an alkoxy; preferably, each of $R^1$, $R^{1a}$, $R^{1b}$, $R^{1c}$ and $R^{1d}$ is independently H, an alkoxy or a halogen; $R^2$ is H, an alkyl or hydroxy.

In a preferred embodiment of the present invention, A is

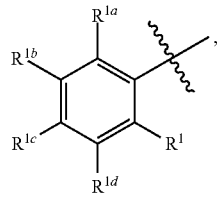

$R^1$, $R^{1a}$, $R^{1b}$ and $R^{1d}$ are H, $R^{1c}$ is H, an alkoxy or a halogen (e.g. H, methoxy or F); $R^2$ is H, an alkyl or hydroxy (e.g. H, methyl or hydroxy).

In a preferred embodiment of the present invention, $R^1$, $R^{1a}$, $R^{1b}$, $R^{1c}$ and $R^{1d}$ are H, $R^2$ is H.

In the process for preparing compound f, the solvent can be a conventional solvent for such cyclization reaction in the art as long as it does not affect the progress of the reaction; preferably, the solvent is an amides solvent and/or a nitriles solvent, such as N,N-dimethylformamide (DMF) and/or acetonitrile. The amount of the solvent is not particularly limited as long as it does not affect the progress of the reaction. The base is preferably an alkali metal carbonate such as potassium carbonate. The amount of the base and compound e can be a conventional amount for such cyclization reaction in the art, and does not need to be particularly limited as long as it does not affect the progress of the reaction. But an excess amount of the base is preferred, that is to say that the molar ratio of the base to compound e is more than 1:1. The temperature of the cyclization reaction can be a conventional temperature for such cyclization reaction in the art, preferably 30-50° C. The progress of the reaction can be monitored by conventional detection method in the art (e.g. TLC, HPLC, GC or HNMR, etc.), preferably disappearance of compound e is seen as completion of the reaction.

In a preferred embodiment of the present invention, the process for preparing compound f preferably comprises mixing a mixture of the base and the solvent, with a mixture of compound e and the solvent to conduct the reaction. Preferably, the mixture of compound e and the solvent is added to the mixture of the base and the solvent.

The process for preparing compound f can further comprise a post-treatment after completion of the cyclization reaction. The post-treatment can be a conventional post-treatment process in the art such as recrystallization. The solvent for recrystallization is preferably an ethers solvent (preferably MTBE), a nitriles solvent (preferably acetonitrile), an esters solvent (preferably ethyl acetate), a mixed solvent of an ethers solvent and an alkanes solvent, a mixed solvent of a nitriles solvent and an alkanes solvent, or a mixed solvent of an esters solvent and an alkanes solvent. The alkanes solvent can be a conventional alkanes solvent in the art, such as a $C_5$-$C_8$ alkanes solvent. The recrystallization temperature is preferably 0 to 60° C. (e.g. 30 to 50° C.). The recrystallization temperature is usually used to provide heat to accelerate the dissolution rate of the substance and increase the solubility of the substance in the solvent, which can be selected according to an actual need. The amount of the solvent for recrystallization is not particularly limited and can be selected according to an actual need. The number of times of the recrystallization can be selected according to an actual need, such as 1-5 time(s).

Before the recrystallization, the reaction solution after completion of the cyclization reaction can be filtered or extracted depending on the reaction solvent.

For example, when the reaction solvent is an amides solvent, g the reaction solution after completion of the cyclization reaction can be extracted before the recrystallization. When the reaction solvent is a nitriles solvent, the reaction solution after completion of the cyclization reaction can be filtered before the recrystallization.

In a preferred embodiment of the present invention, the solvent used in the extracting operation is a conventional solvent in the art such as a haloalkanes solvent (preferably dichloromethane), an ethers solvent (preferably MTBE) or an esters solvent (preferably ethyl acetate).

The organic layer obtained from extracting the reaction solution after completion of the cyclization reaction can be evaporated under reduced pressure to remove a portion of the extracted organic solvent or evaporated to dryness under reduced pressure, and then conducting recrystallization.

The present invention preferably comprises the following steps:

step (a): extracting the reaction solution after completion of the cyclization reaction to give an organic layer, in which a portion of organic solvent is removed to give a mixture A; wherein the solvent for extraction is a haloalkanes solvent (preferably dichloromethane), an ethers solvent (preferably MTBE) or an esters solvent (preferably ethyl acetate); the volume/mass ratio of the mixture A to compound e is preferably 1 mL/g;

step (b): mixing the mixture A obtained in step (a) and an organic solvent, recrystallizing and filtering; wherein the organic solvent is preferably the same as the solvent for recrystallization defined as above.

In a preferred embodiment of the present invention, step (b) is preferably conducted under the protection of a gas (e.g. nitrogen).

The post-treatment of the process for preparing compound f preferably comprises the following steps:

step (i): mixing the reaction solution after completion of the cyclization reaction and water (preferably the reaction solution is added to water), extracting with an organic solvent (e.g. an ethers solvent which is preferably MTBE, or an esters solvent which is preferably ethyl acetate), washing the organic layer with brine, drying (e.g. anhydrous sodium sulfate) and evaporating under reduced pressure to give a mixture A with a volume of 1V (1V refers to the volume/mass ratio of the mixture A to compound e is 1 mL/g, for example, when compound e is 100 g, 1V is 100 mL);

step (ii): under the protection of a gas (e.g. nitrogen), mixing the mixture A obtained in step (i) and an organic solvent (e.g. an ethers solvent or a mixed solvent of an ethers solvent and an alkanes solvent, preferably MTBE), filtering, washing the filter cake with an organic solvent (e.g. an ethers solvent or a mixed solvent of an ethers solvent and an alkanes solvent, preferably MTBE) and drying (e.g. vacuum drying). Wherein, the temperature of the mixing is preferably 0 to 60° C. (e.g. 30 to 50° C.). The temperature of the filtering is preferably −5 to 5° C., for example, 0 to 5° C.

In a preferred embodiment of the present invention, in the process for preparing compound f, compound f1, the isomer of compound f, is simultaneously obtained, that is to say that the process for preparing compound f1 is the same to that of compound f. Compound f1 is shown below,

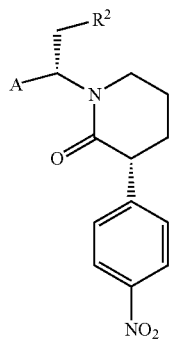

wherein A and R² are defined as above.

In the present invention, the physical properties of compound f and compound f1 are quite different, both of which cannot be crystallized in a solvent like ethanol or acetone, and there is no difference in crystallinity between them.

However, the solubility of compound f is lower than that of compound f1 in a specific solvent, and compound f can precipitate as a solid. Additionally, the inventors of the present invention have also found that when compound f continuously precipitates from the mixture of compound f and compound f1, compound f1 continuously converts to compound f to achieve a dynamic equilibrium. If compound f precipitates, compound f can be isolated by filtration directly, and compound f1 remains in the mother liquor. In a preferred embodiment of the present invention, compound f1 contained in the mother liquor is partially converted to compound f through conventional isomerization methods in the art (e.g., in the presence of an acid or a base, wherein the acid or the base can be conventional acid or base in the isomerization methods in the art as long as compound f1 can be isomerized). When the molar ratio of compound f to compound f1 contained in a mixture is 1:1, the mixture is represented by compound ff. Compound f can be further obtained from the mixture of compound f and compound f1 through the post-treatment of the cyclization reaction. The above steps can be repeated until all or most of compound ft is converted to compound f, thereby the total yield is further increased. Compound ff is shown below,

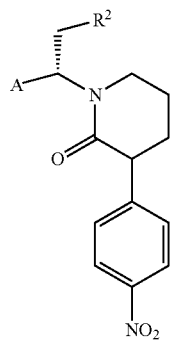

wherein, A and R² are defined as above.

The present invention also provides a process for preparing compound f, which comprises precipitating a solid from a mixed solution formed by the mixture containing compound f and compound f1 with a solvent; the solvent is selected from the group consisting of a nitriles solvent, an esters solvent, an ethers solvent, a mixed solvent of an ethers solvent and an alkanes solvent, a mixed solvent of a nitriles solvent and an alkanes solvent, and a mixed solvent of an esters solvent and an alkanes solvent; wherein, the nitriles solvent can be a conventional nitriles solvent in the art, preferably acetonitrile; the esters solvent can be a conventional esters solvent in the art, preferably ethyl acetate; the ethers solvent can be a conventional ethers solvent in the art, preferably MTBE; the alkanes solvent can be a conventional alkanes solvent in the art, preferably a $C_5$-$C_8$ alkanes solvent;

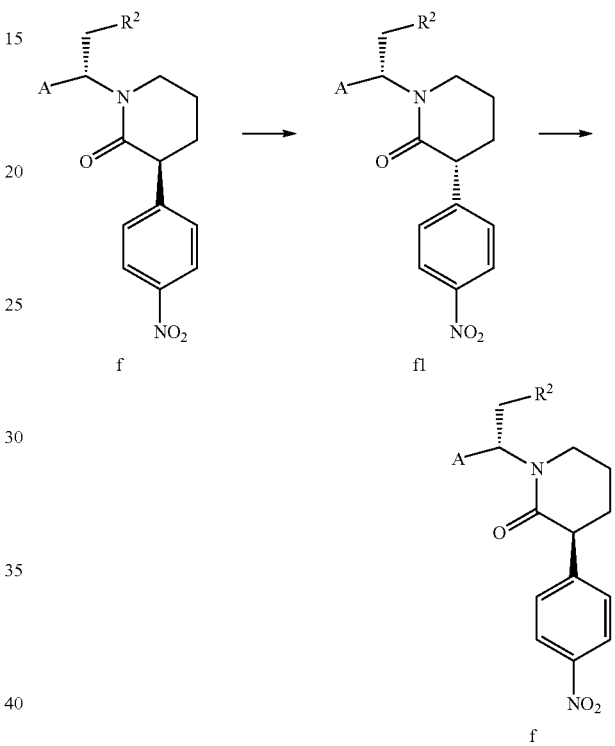

wherein, A and R² are defined as above.

The molar ratio of compound f to compound f1 in the mixture containing compound f and compound f1 can be present in any ratio, preferably 1:2 to 2:1, and the molar ratio can be determined by conventional detection methods such as HPLC and TLC. The mixture containing compound f and compound f1 can be composed of compound f and compound f1, or the amount of compound f and compound f1 determined by HPLC can be 70% or more of the mixture (e.g. 75% or more, 80% or more, 85% or more, 90% or more, 95% or more, 99% or more). If the mixture contains other substances besides compound f and compound f1, as long as the substance does not affect the precipitation of compound f from the solvent. The mixture containing compound f and compound f1 is preferably mixed with the solvent at 0° C. to the reflux temperature of the solvent under normal pressure, preferably 30° C. to the reflux temperature of the solvent under normal pressure, more preferably at 30 to 50° C. The temperature for precipitating a solid is preferably the temperature of an ice bath to room temperature (e.g. −5 to 30° C.), more preferably −5 to 5° C. The time from the mixture containing compound f and compound f1 and the solvent to precipitating a solid is not particularly limited. The mixture containing compound f and compound f1 is preferably mixed with the solvent under the protection of a gas such as nitrogen. In the mixed solution formed by the mixture containing compound f and compound f1 with a solvent, the amount of the solvent is not particularly limited as long as compound f can precipitate as a solid at the temperature of an ice bath to room temperature. If the amount of the solvent is excess, preferably removing a portion of solvent so that compound f precipitates as a solid at the temperature of an ice bath to room temperature (e.g. −5 to 30° C., preferably −5 to 5° C.), the method of removing the solvent can be a conventional method for removing solvent in the art such as vacuum distillation.

The process for preparing compound f can further comprise a post-treatment. The post-treatment can be a conventional post-treatment process in the art, preferably comprises filtering the reaction solution after completion of the reaction (the filtration is preferably conducted at 0° C. to room temperature), and washing the filter cake (the solvent used to wash the filter cake is preferably the solvent used in the precipitation).

The process for preparing compound f can further comprise recrystallizing the precipitated solid. The process for preparing the mixture containing compound f and compound f1 is the same to that of the process for preparing compound f defined as above. The solvent for recrystallization is preferably an ethers solvent (preferably MTBE), a nitriles solvent (preferably acetonitrile), an esters solvent (preferably ethyl acetate), a mixed solvent of an ethers solvent and an alkanes solvent a mixed solvent of a nitriles solvent and an alkanes solvent, or a mixed solvent of an esters solvent and an alkanes solvent. The alkanes solvent can be a conventional alkanes solvent in the art, such as a $C_5$-$C_8$ alkanes solvent. The recrystallization temperature is preferably 0° C. to the reflux temperature of the solvent under normal pressure, more preferably 0 to 60° C. (e.g. 30 to 50° C.). The recrystallization temperature is usually used to provide heat to accelerate the dissolution rate of the substance and increase the solubility of the substance in the solvent, which can be selected according to an actual need. The amount of the solvent for recrystallization is not particularly limited and can be selected according to an actual need. The number of times of the recrystallization can be selected according to an actual need, such as 1 to 5 time(s).

In a preferred embodiment of the present invention, in the process for preparing compound f, when the solvent for precipitating a solid or recrystallization is a mixed solvent of an ethers solvent and an alkanes solvent, a mixed solvent of a nitriles solvent and an alkanes solvent, or a mixed solvent of an esters solvent and an alkanes solvent, the amount of each solvent in the mixed solvent is not particularly limited and can be adjusted according to an actual need, as long as compound f can precipitate as a solid at the temperature of an ice bath to room temperature (e.g. −5° to 30° C., preferably −5° C. to 5° C.).

The process for preparing compound f can further comprise conducting an amidation reaction of compound c or an acidic salt of compound c and compound d in a solvent in the presence of a condensing agent to give compound e as shown below;

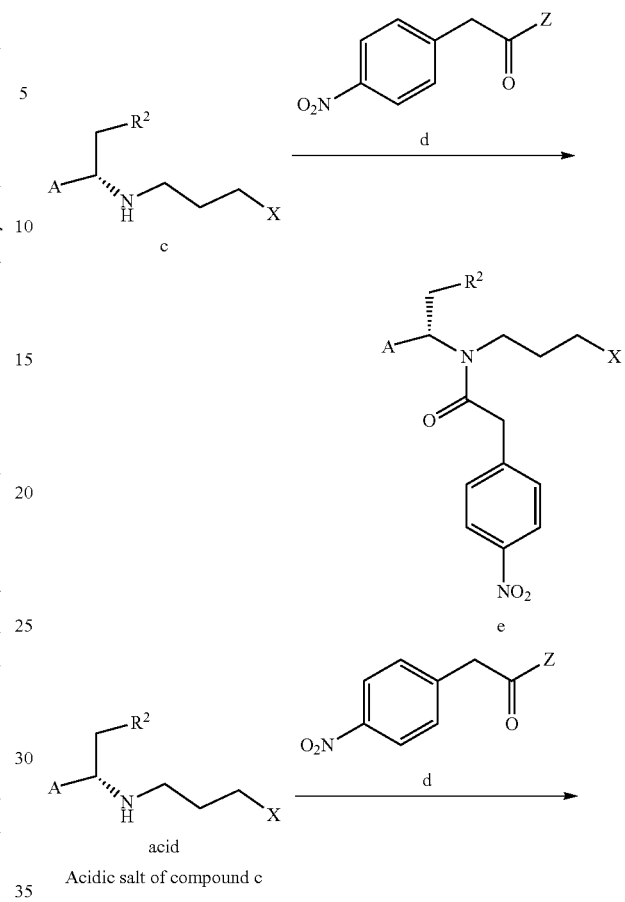

A and $R^2$ are defined as above, X is a leaving group, preferably a halogen (e.g. Cl, Br or I), methanesulfonyloxy or p-toluenesulfonyloxy; Z is a leaving group, preferably hydroxy, a halogen (e.g. F, Cl, Br or I), an alkoxy, pyrrolidin-2,5-dione-1-oxy

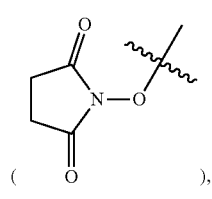 [SMILES: *ON1C(=O)CCC1=O]

isoindole-1,3-dione-2-oxy

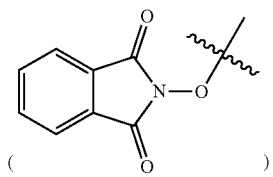 [SMILES: *ON1C(=O)c2ccccc2C1=O]

or 1H-benzotriazol-1-oxy

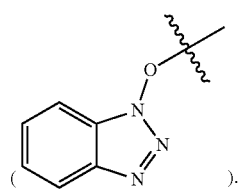 [SMILES: *On1nnc2ccccc21]

In the process for preparing compound e, the solvent can be a conventional solvent for such amidation reaction in the art, preferably a haloalkanes solvent and/or an esters solvent, for example, dichloromethane (DCM) and/or isopropyl acetate.

The amount of the solvent is not particularly limited as long as it does not affect the progress of the reaction. The condensing agent can be a conventional condensing agent for such amidation reaction in the art, preferably N,N'-carbonyldiimidazole (CDI) or 2-(7-azabenzotriazol-1-yl)-N,N,N',N'-tetramethyluronium hexafluorophosphate (HATU). The amount of the condensing agent and compound c can be a conventional amount for such reaction in the art, and does not need to be particularly limited as long as it does not affect the progress of the reaction. The amount of compound c and compound d, or the acidic salt of compound c and compound d can be a conventional amount for such amidation reaction in the art, and does not need to be particularly limited as long as it does not affect the progress of the reaction. The temperature of the amidation reaction can be a conventional temperature for such amidation reaction in the art, preferably −5 to 5° C., such as 0 to 5° C. The progress of the reaction can be monitored by conventional detection method in the art (e.g. TLC, HPLC, GC or HNMR, etc.), preferably disappearance of compound c is seen as completion of the reaction.

In a preferred embodiment of the present invention, the process for preparing compound e preferably comprises mixing a mixed solution of the acidic salt of compound c or compound c, compound d and the solvent, and a mixed solution of the condensing agent and the solvent at −5 to 5° C. (e.g. 0 to 5° C.) to conduct the reaction. Preferably, the mixed solution of the condensing agent and the solvent is added dropwise to the mixed solution of the acidic salt of compound c or compound c, compound d and the solvent.

The process for preparing compound e can further comprise a post-treatment after completion of the amidation reaction. The post-treatment can be a conventional post-treatment process in the art. The post-treatment of the present invention preferably comprises adjusting the pH value of the reaction solution to 1 after completion of the amidation reaction, followed by washing the organic layer with a saturated aqueous sodium bicarbonate solution and water, and evaporating the organic layer to dryness under reduced pressure.

The process for preparing compound f can further comprise conducting a substitution reaction of compound a and compound b to give compound c as shown below;

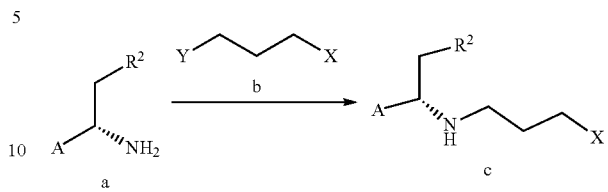

A and $R^2$ are defined as above, each of X and Y is a leaving group independently selected from the group consisting of a halogen (e.g. Cl, Br or I), methanesulfonyloxy or p-toluenesulfonyloxy, wherein Y is easier to leave than X.

In the present invention, compound c can be prepared using the method disclosed by *Journal of Organic Chemistry*, 77(16), 7028-7045, 2012.

The present invention also provides a compound selected from the group consisting of compound e, compound f, compound g, compound f1 and compound ff;

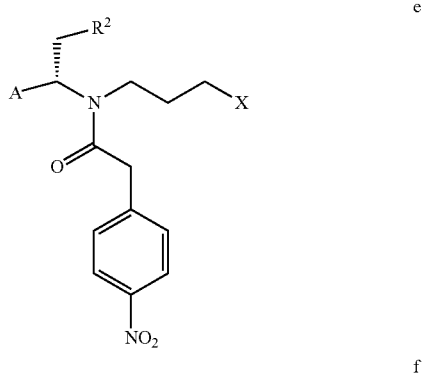

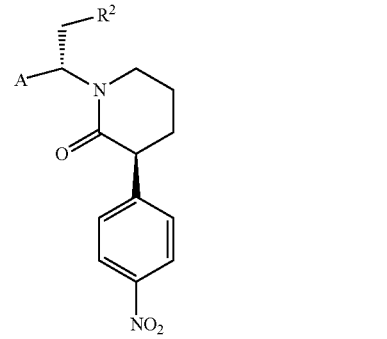

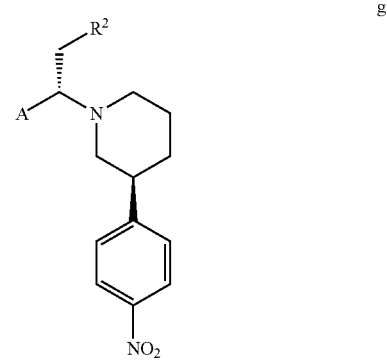

fl
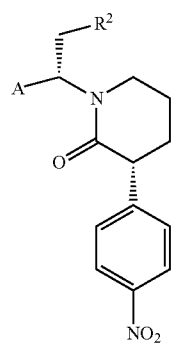
ff
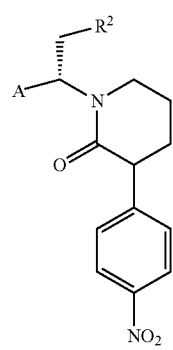
wherein, X, A and $R^2$ are defined as above.
Compound e is preferably selected from the group consisting of
NIR10A
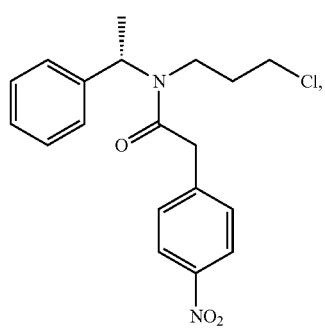
NIR10B
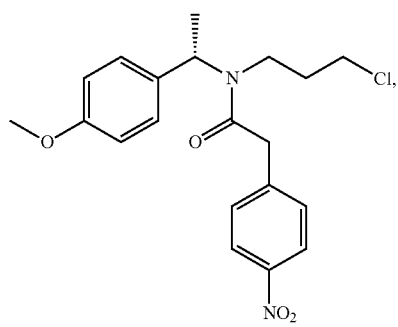
NIR10C
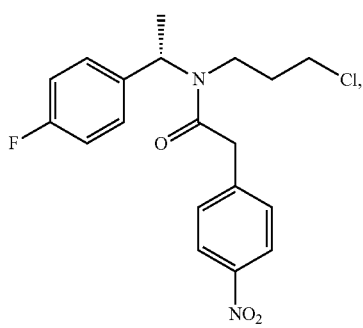
NIR10D
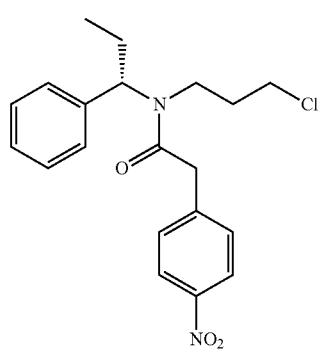
and
NIR10E
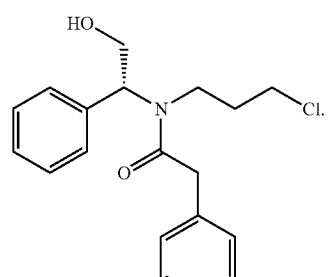
Compound f is preferably selected from the group consisting of
NIR30A
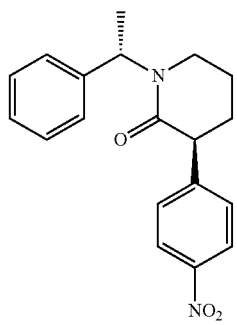

-continued

NIR30B

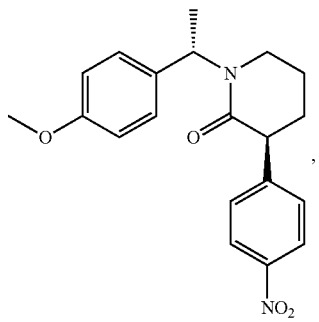,

NIR30C

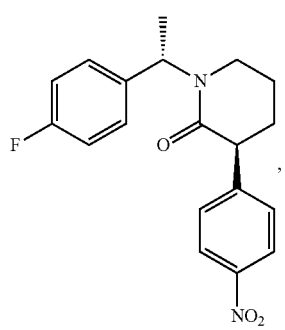,

NIR30D

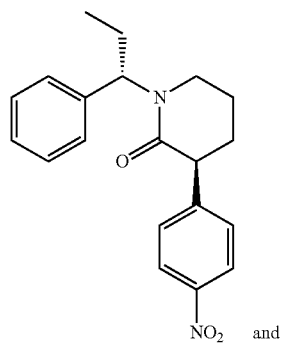 and

NIR30E

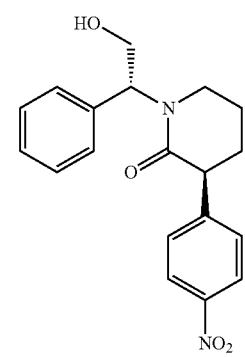

Compound g is preferably

NIR40A

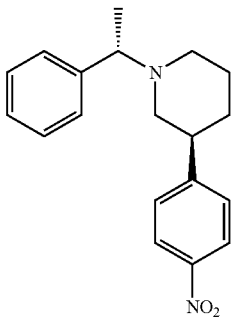

The present invention also provides a process for preparing (S)-4-(piperidin-3-yl)aniline, which comprises conducting a hydrogenation reaction of compound g in a solvent in the presence of Pd/C and hydrogen to give (S)-4-(piperidin-3-yl)aniline as shown below;

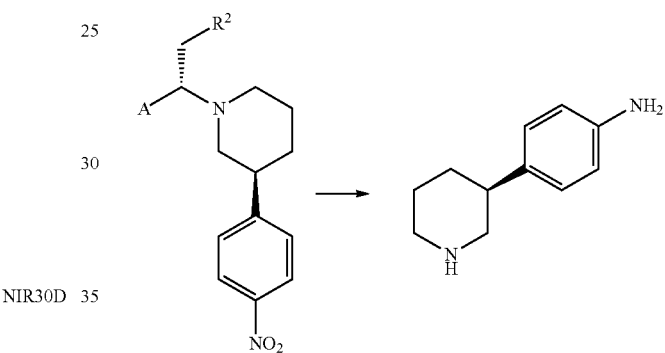

g

X, A and $R^2$ are defined as above.

In the process for preparing (S)-4-(piperidin-3-yl)aniline, the solvent can be a conventional solvent for such hydrogenation reaction in the art, preferably an alcohols solvent. The alcohols solvent is preferably selected from the group consisting of methanol, ethanol, n-propanol, isopropanol, n-butanol, isobutanol and tert-butanol, more preferably methanol. The amount of the solvent is not particularly limited as long as it does not affect the progress of the reaction. The Pd/C is preferably palladium hydroxide on carbon, more preferably 20% palladium hydroxide on carbon (20% refers to the ratio of the mass of palladium hydroxide relative to the total mass of palladium hydroxide and carbon). When Pd/C is palladium hydroxide on carbon, the hydrogenation reaction is preferably conducted in the presence of acetate acid.

The reaction pressure is a conventional pressure for such hydrogenation reaction in the art, preferably 1.0 to 1.5 Mpa. The reaction temperature can be a conventional temperature for such hydrogenation reaction in the art, preferably 45 to 50° C. The progress of the reaction can be monitored by conventional detection method in the art (e.g. TLC, HPLC, GC or HNMR, etc.), preferably disappearance of compound g is seen as completion of the reaction.

In the process for preparing (S)-4-(piperidin-3-yl)aniline, preferably purging the reaction system with hydrogen (e.g. three times) and pressurizing (e.g. 1.0 Mpa to 1.5 Mpa) before conducting the hydrogenation reaction.

The process for preparing (S)-4-(piperidin-3-yl)aniline preferably comprises mixing compound g and the solvent, adding Pd/C, purging the reaction system with hydrogen and pressurizing to conduct the hydrogenation reaction.

The process for preparing (S)-4-(piperidin-3-yl)aniline can further comprise a post-treatment after completion of the hydrogenation reaction. The post-treatment can be a conventional post-treatment process in the art. The post-treatment of the present invention preferably comprises isolating the liquid from the reaction solution after completion of the reaction by solid-liquid separation (e.g. filtration), removing the solvent of the liquid (e.g. evaporating under reduced pressure) to give product 1; mixing the product 1 with water, adjusting the pH to 10 (e.g. 30% aqueous alkali solution), extracting (e.g. the extracting times can be 1-2) with an organic solvent (e.g. ethyl acetate), washing the organic layer with brine, removing the solvent (e.g. evaporating under reduced pressure) to give product 2; recrystallizing the product 2 (the solvent for recrystallization is preferably a mixed solvent of ethyl acetate and n-heptane) and drying the obtained solid (e.g. vacuum drying).

The process for preparing (S)-4-(piperidin-3-yl)aniline can further comprise conducting a reduction reaction of compound f in a solvent in the presence of an alkali metal borohydride as a reducing reagent and a Lewis acid under the protection of a gas to give compound g as shown below;

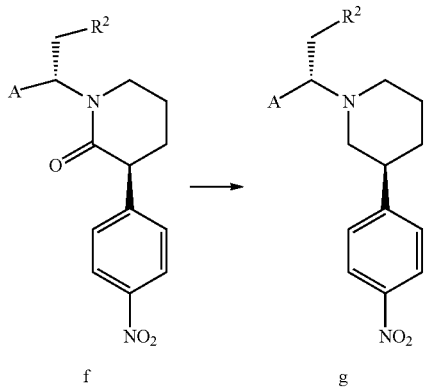

A and $R^2$ are defined as above.

In a preferred embodiment of the present invention, compound f can be prepared using the above methods.

In the process for preparing compound g, the protection gas is provided by a gas as long as the gas can replace the air in the reaction system and does not affect the progress of the reaction, which is preferably nitrogen. The solvent can be a conventional solvent for such reduction reaction in the art, preferably an ethers solvent. The ethers solvent is preferably tetrahydrofuran. The amount of the solvent is not particularly limited as long as it does not affect the progress of the reaction. The Lewis acid is preferably aluminium trichloride. The reducing reagent is preferably sodium borohydride. The amount of the Lewis acid and the reducing reagent can be a conventional amount for such reduction reaction in the art, and does not need to be particularly limited as long as it does not affect the progress of the reaction. The amount of compound f and the reducing reagent can be a conventional amount for such reduction reaction in the art, and does not need to be particularly limited as long as it does not affect the progress of the reaction. The reaction temperature can be a conventional temperature for such reduction reaction in the art, preferably 0 to 30° C. (e.g. under an ice bath). The progress of the reaction can be monitored by conventional detection method in the art (e.g. TLC, HPLC, GC or HNMR, etc.), preferably disappearance of compound f is seen as completion of the reaction.

In a preferred embodiment of the present invention, the process for preparing compound g preferably comprises mixing a mixture of the solvent, the Lewis acid and the reducing reagent, with a mixture of compound f and the solvent at −5 to 5° C. (e.g. 0° C.) under the protection of the gas to conduct the reduction reaction. Wherein, the mixture of the solvent, the Lewis acid and the reducing reagent is preferably prepared by adding the Lewis acid to the solvent in portions at −5 to 5° C. (e.g. 0° C.), followed by adding the reducing reagent in portions at −5 to 5° C. (e.g. 0° C.) under nitrogen atmosphere.

The process for preparing compound g can further comprise a post-treatment after completion of the reduction reaction. The post-treatment can be a conventional post-treatment process in the art. The post-treatment of the present invention preferably comprises mixing the reaction solution with aqueous hydrochloric acid solution after completion of the reduction reaction (the aqueous hydrochloric acid solution can be prepared by adding 400 g water to 235 g concentrated hydrochloric acid), adding water, adjusting pH to 11 to 12 (e.g. 30% aqueous alkali solution), extracting with an organic solvent (e.g. extracting twice with ethyl acetate), washing the organic layer with brine, evaporating to dryness under reduced pressure.

The present invention also provides a process for preparing compound h, which comprises reacting (S)-4-(piperidin-3-yl)aniline with an amino-protecting reagent to give compound h as shown below; wherein the process for preparing (S)-4-(piperidin-3-yl)aniline is defined as above;

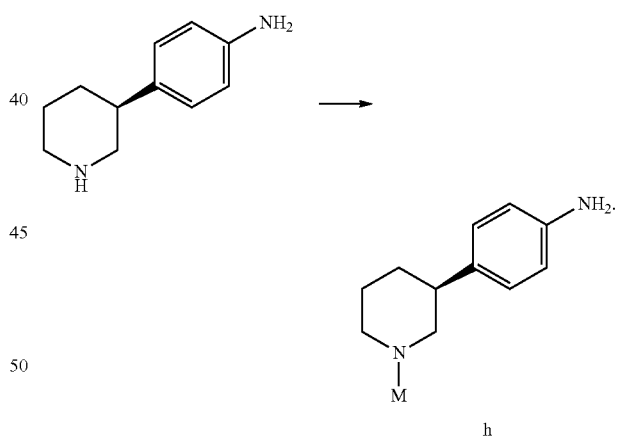

wherein, M is a conventional amino-protecting group in the art, such as an alkoxycarbonyl amino-protecting group (e.g. Boc, Cbz, Fmoc, Alloc, Teoc, methoxycarbonyl or ethoxycarbonyl) or an acyl amino-protecting group (e.g. Pht, Tos or Tfa).

In the process for preparing compound h, the solvent can be a conventional solvent for such reaction in the art, preferably a haloalkanes solvent such as dichloromethane (DCM). The amount of the solvent is not particularly limited as long as it does not affect the progress of the reaction. The amino-protecting reagent can be a conventional amino-protecting reagent for such reaction in the art. The amount of (S)-4-(piperidin-3-yl)aniline and the amino-protecting reagent can be a conventional amount for such reaction in the art, and does not need to be particularly limited as long as it does not affect the progress of the reaction. The reaction temperature can be a conventional temperature for such reaction in the art, preferably −5 to 5° C. (e.g. 0° C.). The progress of the reaction can be monitored by conventional detection method in the art (e.g. TLC, HPLC, GC or HNMR, etc.), preferably disappearance of (S)-4-(piperidin-3-yl)aniline is seen as completion of the reaction.

In a preferred embodiment of the present invention, the process for preparing compound h preferably comprises mixing a mixture of the (S)-4-(piperidin-3-yl)aniline and the solvent, with a mixture of the amino-protecting reagent and the solvent to conduct the reaction. Preferably, the mixture of the amino-protecting reagent and the solvent is added to the mixture of the (S)-4-(piperidin-3-yl)aniline and the solvent.

The process for preparing compound h can further comprise a post-treatment after completion of the reaction. The post-treatment can be a conventional post-treatment process in the art. The post-treatment of the present invention preferably comprises mixing the reaction solution with water after completion of the reaction, stirring and heating to 15 to 25° C., isolating the organic layer, followed by evaporating (e.g. the evaporating temperature is preferably 45 to 50° C.) under reduced pressure to give a concentrated liquor 1 with a volume of 1V (1V refers to the volume/mass ratio of concentrated liquor 1 to (S)-4-(piperidin-3-yl)aniline is 1 mL/g, for example, when (S)-4-(piperidin-3-yl)aniline is 100 g, 1V is 100 mL); then mixing the concentrated liquor 1 with an alcohols solvent (e.g. isopropanol), stirring (the stirring is preferably conducted at 55 to 60° C.) until the solution becomes clarified, followed by mixing with water, stirring (the stirring is preferably firstly conducted at 55 to 60° C., followed by stirring at −5-=to 5° C. such as 0° C.), filtering (the filtering is preferably conducted at −5 to 5° C. such as 0° C.), washing the filter cake with a mixed solvent of water and an alcohols solvent (e.g. isopropanol), and drying (e.g. vacuum drying).

In the present invention, the process for preparing (S)-4-(piperidin-3-yl)aniline is preferably as shown below:

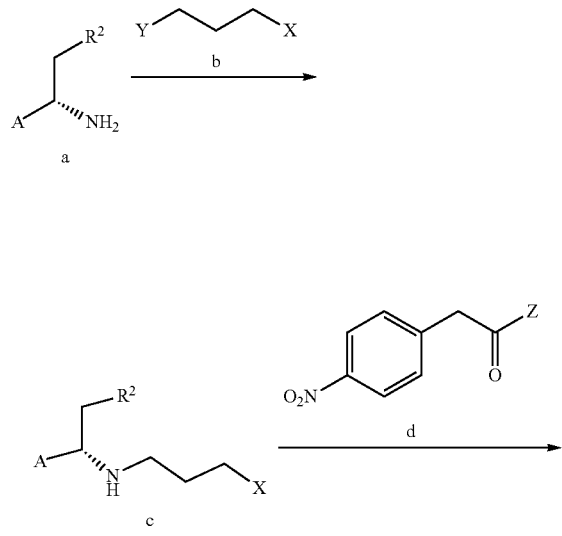

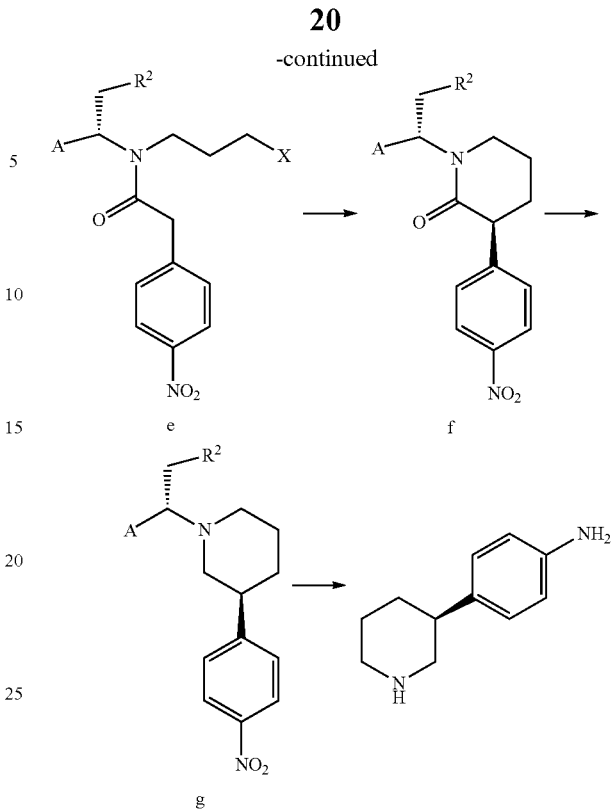

In the present invention, the term alkyl is preferably $C_1$-$C_4$ alkyl, such as methyl, ethyl, n-propyl, isopropyl, n-butyl, isobutyl or tert-butyl.

In the present invention, the term alkoxy is preferably $C_1$-$C_4$ alkoxy, such as methoxy, ethoxy, n-propoxy, isopropoxy, n-butoxy, isobutoxy or tert-butoxy.

In the present invention, unless otherwise specified, the term halogen is preferably Cl, Br or I.

In the present invention, the term aryl is preferably $C_6$-$C_{20}$ aryl, more preferably $C_6$-$C_{14}$ aryl. Wherein the aryl refers to any stable monocyclic or bicyclic carbon ring which can have up to 7 atoms in each ring, and at least one ring is aromatic. Examples of the above aryl include phenyl, naphthyl, tetrahydronaphthyl, 2,3-dihydroindenyl, biphenyl, phenanthryl, anthryl or acenaphthyl. It is to be understood that when the aryl is a bicyclic substituent and one of the rings is non-aromatic, the linkage is made through the aromatic ring.

In the present invention, the term heteroaryl is preferably $C_2$-$C_{10}$ heteroaryl having 1 to 4 heteroatom selected from the group consisting of O, N and S, more preferably $C_2$-$C_6$ heteroaryl having 1 to 4 heteroatom selected from the group consisting of O, N and S. The heteroaryl refers to a stable monocyclic ring or bicyclic ring which can have up to 7 atoms in each ring, and at least one of the rings is an aromatic ring having 1 to 4 heteroatom selected from the group consisting of O, N and S.

In the present invention, the "optionally substituted" refers to that the aryl or the heteroaryl is substituted or unsubstituted, when the aryl or the heteroaryl is substituted, the number of the substituent(s) can be adjusted according to the number of position for substitution.

The term "aryloxy" refers to an aryl having a specific number of carbon atoms connecting to another group through an oxygen bridge. The term "aryloxy" contains the definition of the above aryl.

The term "cycloalkyl" refers to a monocyclic or polycyclic hydrocarbon group, wherein each ring may have one or more than one double bonds, but there is no ring having a fully conjugated 7-electron system. The cycloalkyl is preferably a cycloalkyl having 1 to 3 rings formed by 3 to 20 carbon atoms, more preferably 3 to 10 carbon atoms. Examples of the cycloalkyl include, but are not limited to cyclopropyl, cyclobutyl, cyclopentyl, cyclohexyl, cycloheptyl, cyclooctyl, cyclodecyl, cyclododecyl or cyclohexenyl. In the present invention, the cycloalkyl can be substituted by 1 to 4 substituent(s) selected from the group consisting of deuterium, a halogen, an alkyl, an alkoxy, hydroxy, an aryl, an aryloxy, a cycloalkyl, an acylamido, oxo, amino, nitro, cyano and mercapto. When the number of the substituents is 2, 3 or 4, the substituents can be identical or different.

The term "cycloalkenyl" refers a monocyclic or polycyclic hydrocarbon group, wherein each ring may have one or more than one double bonds, but there is no ring having a fully conjugated 7-electron system. The cycloalkenyl is preferably is preferably a cycloalkenyl having 1 to 3 rings formed by 3 to 20 carbon atoms, more preferably 3 to 10 carbon atoms. Examples of the cycloalkenyl include, but are not limited to cyclopropenyl, cyclobutenyl, cyclopentenyl, cyclohexenyl, cycloheptenyl, cyclooctenyl, cyclodecenyl, and cyclododecenyl. The cycloalkenyl can be substituted by the substituent(s) (the number of the substituent(s) is preferably 1 to 4) selected from the group consisting of deuterium, halogen, alkyl, alkoxy, hydroxy, aryl, aryloxy, cycloalkyl, acylamido, oxo, amino, nitro, cyano and mercapto. When the substituent of the cycloalkenyl locates at a carbon-carbon double bond and makes the double bond saturated, a cycloalkyl group can be formed.

The term "heterocycloalkyl" used alone or as part of another group, refers to a 4 to 12 membered monocyclic or polycyclic group having 1 to 4 heteroatoms (the heteroatom is preferably selected from the group consisting of nitrogen, oxygen and sulfur), wherein each ring may have one or more than one double bonds, but there is no ring having a fully conjugated π-electron system. The heterocycloalkyl can be substituted by 1 to 4 substituent(s), the substituent(s) can be selected from the group consisting of, for example, an alkyl, a halogen and oxo. Furthermore, any ring of the heterocycloalkyl can be fused to a cycloalkyl, an aryl, a heteroaryl or a heterocycloalkyl. Examples of the heterocycloalkyl include, but are not limited to oxazolinyl, oxetanyl, pyranyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridyl, dihydropyrimidinyl, dihydropyrrolyl, dihydrotetrazolyl, dihydrothiadiazolyl, dihydrothiazolyl, dihydrothienyl, dihydrotriazolyl, dihydroazetidinyl, tetrahydrofuranyl and tetrahydrothiophenyl and the N-oxide thereof. The heterocycloalkyl can connect to another group via a carbon atom or a heteroatom thereof.

The term "alkenyl" refers to a linear, branched or cyclic non-aromatic hydrocarbon group having a specific number of carbon atoms and at least one carbon-carbon double bond. Preferably one carbon-carbon double bond is present, and up to four non-aromatic carbon-carbon double bonds can be present. In the present invention, the term alkenyl refers to $C_2$-$C_{12}$ alkenyl, preferably $C_2$-$C_6$ alkenyl, including ethenyl, propenyl, butenyl, 2-methylbutenyl and cyclohexenyl. The linear, branched or cyclic part of the alkenyl can contain a double bond. If the alkenyl is substituted, the substituent(s) (the number of the substituent(s) is preferably 1 to 4) can be independently selected from the group consisting of an alkyl, a halogen, an alkoxy, hydroxy, an aryl, an aryloxy, a cycloalkyl, an acylamido, an acyl, amino, nitro, nitrile and mercapto. When the number of the substituents is 2, 3 or 4, the substituents can be identical or different.

The term "alkynyl" refers to a linear, branched or cyclic hydrocarbon group having a specific number of carbon atoms and at least one carbon-carbon triple bond. Up to three carbon-carbon triple bonds can be present. In the present invention, the term alkynyl is preferably $C_2$-$C_{12}$ alkynyl, more preferably $C_2$-$C_6$ alkynyl, including ethynyl, propynyl, butynyl, 3-methylbutynyl and the like.

The term "acyl" refers to carbonyl or formyl, when each of the two sides of acyl is substituted, carbonyl

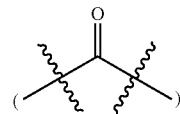 [SMILES: *C(*)=O]

is formed; when only one of the two sides of acyl is substituted, formyl

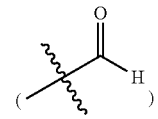 [SMILES: *C=O]

is formed.

The term "acylamido" means carbonyl amido

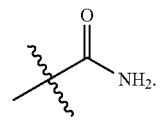 [SMILES: *C(N)=O]

such as

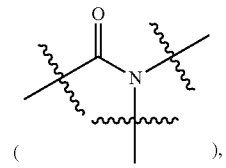 [SMILES: *C(=O)N(*)*]

The term "haloalkyl" refers to an alkyl which is substituted by halogen at any position. The term "haloalkyl" contains the definitions of the above halogen and alkyl.

Without violating the common knowledge in the art, the preferred embodiments of the present invention are obtained by optionally combining the preferred conditions.

The reagents and raw materials used in the present invention are commercially available.

In the present invention, the reflux temperature of a solvent under normal pressure is the temperature at which the solvent is refluxed under standard atmosphere.

In the present invention, room temperature refers to 10 to 30° C., preferably 25° C. The temperature of ice bath refers to −5 to 5° C., preferably 0° C. Overnight refers to 8 to 16 hours, preferably 12 hours.

The positive and progressive effects of the present invention are that the process of the present invention does not involve the steps of catalytic reduction or catalytic coupling reaction of precious metals and chiral separation, which has advantages such as low equipment requirements, simple operation, favorable industrial production, avoiding waste liquid containing heavy metals and phosphorus, low cost and high product ee value.

BRIEF DESCRIPTION OF THE DRAWINGS

FIGS. 1A-1C show TLC plate scanned in fluorescence at different reaction stage of Method 1 of Embodiment 2. Wherein FIG. 1a shows TLC plate of the reaction solution scanned in fluorescence before the start of the reaction, FIG. 1b shows TLC plate of the reaction solution scanned in fluorescence after completion of the reaction, and FIG. 1c shows TLC plate of the obtained yellow solid NIR30A scanned in fluorescence.

DETAILED DESCRIPTION OF THE PREFERRED EMBODIMENT

In the following embodiments, room temperature refers to 10 to 30° C., preferably 25° C. The temperature of ice bath refers to −5 to 5° C., preferably 0° C. Overnight refers to 8 to 16 hours, preferably 12 hours.

Embodiment 1

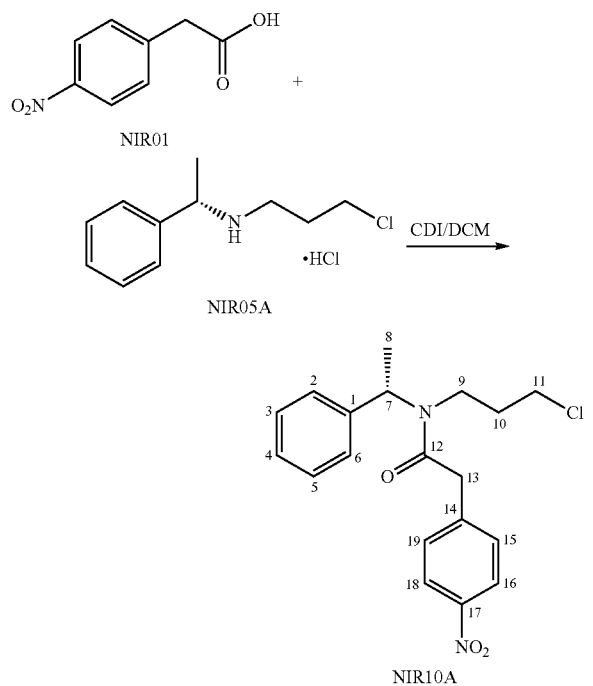

NIR05A was prepared using the method in the reference *Journal of Organic Chemistry*, 77(16), 7028-7045, 2012.

NIR05A (23.4 g), NIR01 (18.1 g) and dichloromethane (100 mL) were successively added into a reaction flask, the mixture was stirred under an ice bath.

A solution of N,N'-carbonyldiimidazole (17.0 g) in dichloromethane was added dropwise to the above mixture. After completion of the reaction, the pH of the reaction solution was adjusted to 1 with dilute hydrochloric acid, the organic layer was washed with saturated sodium bicarbonate solution and water, and evaporated to dryness under reduced pressure to give 32.5 g NIR10A as a red oil with a yield of 90.0%.

NIR10A: $^1$H NMR (400 MHz, in CDCl$_3$, 298K, δ in ppm) δ 1.53, 1.59 (3H, d, d, H-8); 1.47-1.54, 1.84-1.91 (2H, m, m, H10); 3.14-3.50 (4H, m, H9,11); 3.87, 3.92 (2H, s, s, H13); 5.14, 6.03 (1H, t, t, H7); 7.15-7.50 (7H, m, H2,3,4,5,15,19); 8.18-8.20 (2H, m, H16,18). $^{13}$C NMR (100 MHz, in CDCl$_3$, 298K, δ in ppm) δ 16.7, 18.6 (C8); 31.6, 33.4 (C10); 40.5, 41.0 (C13); 41.7, 42.4, 43.2 (C9,11); 51.7, 56.2 (C7); 123.9 (C16,18); 126.7, 127.7, 127.9, 128.1, 128.7, 129.1 (C2-6); 130.2 (C15,19); 139.9, 140.5 (C1); 142.8, 142.9 (C14); 147.1 (C17); 169.8 (C12). MS: 361.1 (M+H).

Embodiment 2

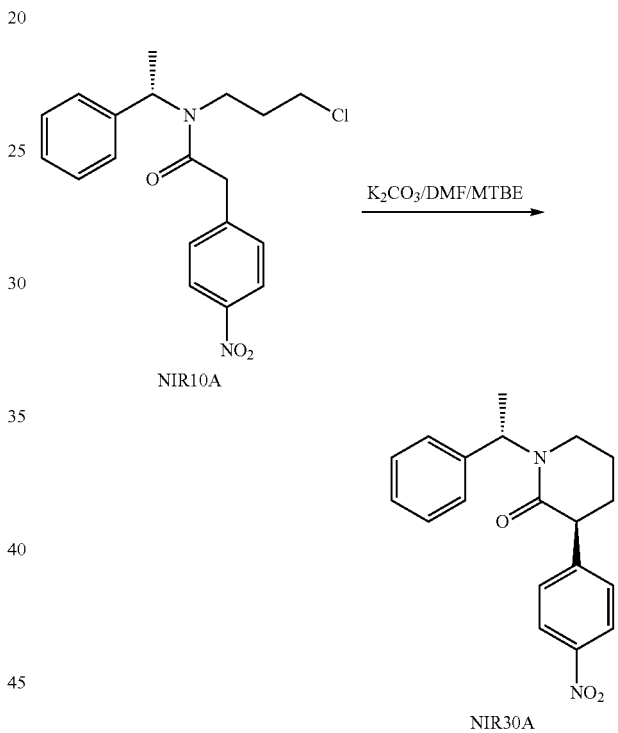

Figure 1A:
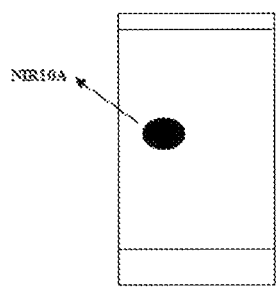
Figure 1B:
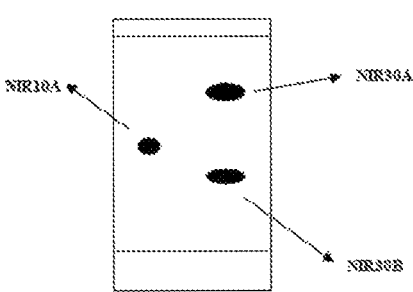
Figure 1C:
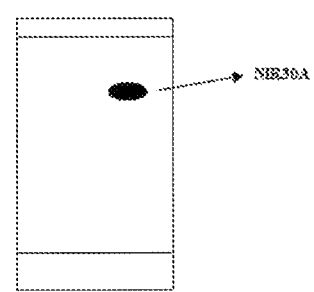

Method 1: Potassium carbonate (7.7 g) and DMF (20 mL) were added into a three-necked reaction flask, and the mixture was maintained at 50° C., followed by addition of a solution of NIR10A (10 g) in DMF (20 mL) under stirring. After completion of the reaction, the reaction solution was added to water and stirred, then extracted with MTBE (30 mL) for three times. The organic phases were combined, washed with brine and dried over anhydrous sodium sulfate. The organic phase was evaporated under reduced pressure to a volume of about 1V (i.e. 10 mL), followed by addition of 40 mL MTBE. The mixture was stirred at 50° C. under nitrogen atmosphere, then gradually cooled to 0° C. and filtered. The filter cake was washed twice with 5 mL MTBE, then dried in vacuum to give 2.7 g NIR30A (de>98%) as a yellow solid with a yield of 30%. TLC determining that NIR10A was no longer reacted was seen as completion of the reaction. The developing solvent for TLC was n-heptane: ethyl acetate=3:1 (V:V). FIGS. 1A-1C show TLC plate scanned in fluorescence at different reaction stage. FIG. 1a shows TLC plate of the reaction solution scanned in fluorescence before the start of the reaction, FIG. 1b shows TLC plate of the reaction solution scanned in fluorescence after completion of the reaction, and FIG. 1c shows TLC plate of the obtained yellow solid NIR30A scanned in fluorescence.

Method 2: NIR10A (2.0 g), potassium carbonate (1.53 g) and DMF (15 mL) were added to a reaction flask, and the reaction solution was stirred at 50° C. for 18 hours. After completion of the reaction, 30 mL water was added the reaction solution, then mixture was stirred, and then extracted twice with ethyl acetate (30 mL*2). The organic phase was washed with brine, dried over anhydrous sodium sulfate and filtered. The filtrate was evaporated under reduced pressure to give a crude product, which was purified by column chromatography (petroleum ether/ethyl acetate=2/1) to give NIR30A (370 mg, 29%) and NIR30B (343 mg, 26%). The structure of compound NIR30B is shown below:

NIR30B

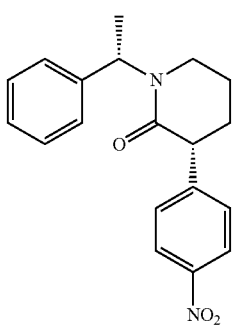

Method 3: Potassium carbonate (24.9 g), acetonitrile (60 mL) was added to a reaction flask, the mixture was warmed to 50° C., followed by addition of a solution of NIR10A (32.5 g) in acetonitrile (65 mL) under stirring. After completion of the reaction, the reaction solution was cooled to room temperature, filtered, and the filter cake was washed with acetonitrile. The filtrate was collected, combined and evaporated to dryness under reduced pressure to give a residue. Ethyl acetate (230 mL) was added to the residue and the mixture was warmed to 50° C. to make the residue dissolved, then cooled to room temperature and filtered. The filter cake was recrystallized once with MTBE (65 mL) (using the same procedure in Method 1) to give 10.4 g NIR30A (de>98%) with a yield of 35%.

NIR30A: $^1$H NMR (400 MHz, in CDCl$_3$, 298K, δ in ppm) δ 1.59 (3H, d); 1.65-1.76 (1H, m); 1.84-1.98 (2H, m); 2.15-2.23 (1H, m); 2.97 (1H, m), 3.29 (1H, m), 3.84 (1H, dd), 6.18 (1H, q), 7.29-7.38 (5H, m), 7.41 (2H, d), 8.20 (2H, d). MS: 325.1 (M+H). [α]$^{25}_D$ –166.1° (c 1.0, CHCl$_3$).

NIR30B: $^1$H NMR (400 MHz, in CDCl$_3$, 298K, δ in ppm) δ 1.58 (3H, d); 1.74-1.91 (3H, m); 2.15-2.23 (1H, m); 2.92 (1H, m), 3.24 (1H, m), 3.84 (1H, dd), 6.18 (1H, q), 7.31-7.41 (7H, m), 8.19 (2H, d). MS: 325.1 (M+H).

Embodiment 3

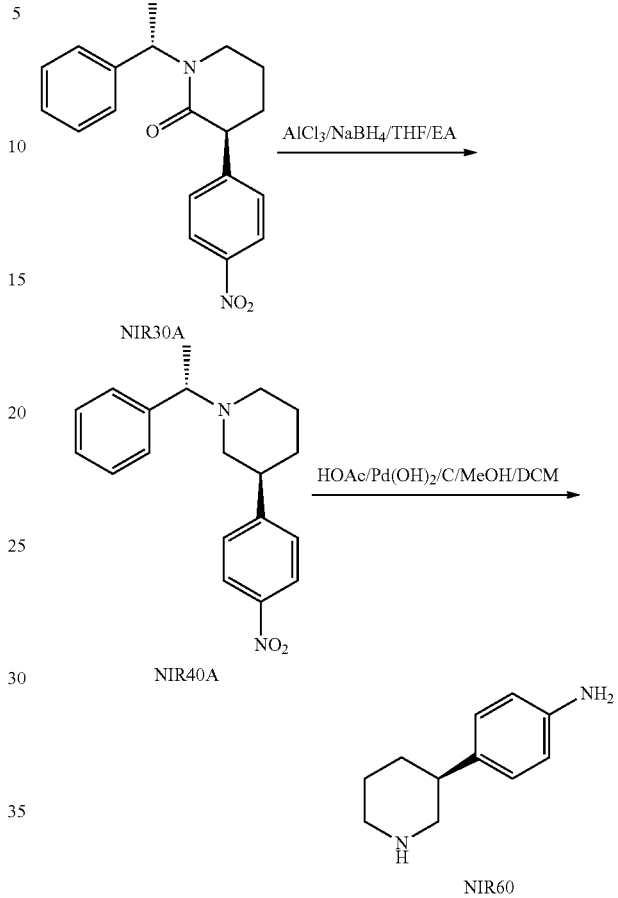

135.9 g anhydrous aluminum trichloride was added in portions to 600 g tetrahydrofuran in a reaction flask under an ice bath and nitrogen atmosphere. The mixture was maintained at 0 to 10° C., then 35 g sodium borohydride was added in portions under nitrogen atmosphere, and the mixture was stirred for 1 hour. A solution of NIR30A (100 g) in 300 g THF was added dropwise to the above mixture under an ice bath. After the dropwise addition, the reaction solution was stirred at room temperature until completion of the reaction.

400 g water and 236 g concentrated hydrochloric acid were added to another reaction flask, and the mixture was cooled to 0 to 5° C. under stirring, followed by dropwise addition of the above reaction solution. After the dropwise addition, the reaction solution was stirred for 1 hour, and then 500 mL water was added. The pH of the mixture was adjusted to 11 to 12 with 30% aqueous NaOH solution, extracted twice with ethyl acetate. The organic phases were combined, washed with brine and evaporated to dryness under reduced pressure to give NIR40A.

NIR40A: $^1$H NMR (400 MHz, in CDCl$_3$, 298K, δ in ppm) δ 1.40 (3H, d), 1.62-1.85 (3H, m), 1.89 (1H, d), 1.96-2.10 (2H, m), 2.83-2.94 (2H, m), 3.03 (1H, d), 3.52 (1H, q), 7.20-7.40 (7H, m), 8.09 (2H, d). MS: 311.2 (M+H).

NIR40A was dissolved in 1100 g methanol, and then added into an autoclave, followed by addition of 10 g 20% palladium hydroxide on carbon and 10 g acetic acid. The autoclave was purged with hydrogen for three times and then pressurized with hydrogen to 1.0 to 1.5 MPa. The reaction solution was stirred at 45 to 50° C. under a pressure of 1.0 to 1.5 MPa. After completion of the reaction, the reaction solution was filtered and the filtrate was evaporated to dryness under reduced pressure to give a residue.

200 g water was added to the residue, and then the pH was adjusted to 10 with 30% aqueous NaOH solution and extracted twice with ethyl acetate. The organic phases were combined, washed with brine and evaporated to dryness under reduced pressure to give a residue, which was recrystallized by a mixed solvent of ethyl acetate and n-heptane, then dried in vacuum to give 30 g NIR 60A with a yield of 55% for two steps, HPLC purity was 97%, ee=98.5%.

NIR60A: $^1$H NMR (400 MHz, in CDCl$_3$, 298K, δ in ppm) δ 1.52-1.59 (2H, m), 1.74-1.78 (1H, m), 1.94-1.96 (1H, m), 2.54-2.63 (3H, m), 3.06-3.12 (2H, m), 6.62 (2H, d), 7.00 (2H, d). MS: 177.2 (M+H).

Embodiment 4

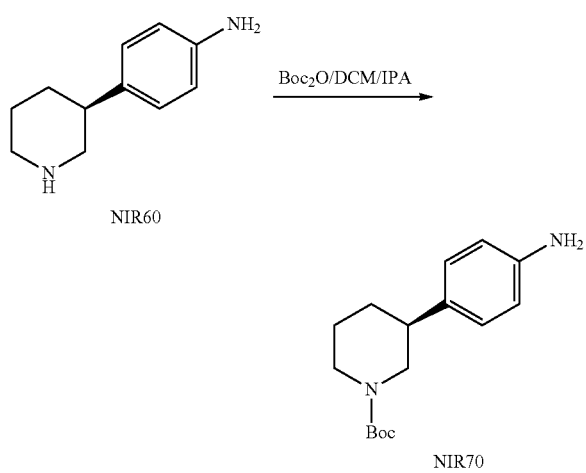

A solution of Boc$_2$O (59.47 g) in dichloromethane (500 mL) was added to a solution of NIR60 (50 g) in dichloromethane (500 mL) under an ice bath. After completion of the reaction, water (500 mL) was added and the mixture was stirred and warmed to 15 to 25° C. The mixture was allowed to stand for partition, and then evaporated under reduced pressure (45 to 50° C.) until the distillate was significantly reduced (about one volume). Then 200 mL isopropanol was added, the mixture was purged with nitrogen and warmed to 55 to 60° C., stirred for half an hour until the mixture became clarified, and stirred for another 2 hours. Subsequently, 400 mL water was slowly added dropwise, and the mixture was stirred for another 5 hours, then gradually cooled to 0° C. and continued stirring. The mixture was filtered at 0° C. and the filter cake was washed twice with water/isopropanol (3/1=V:V), then dried in vacuum to give 66.6 g NIR70 as a pink solid with a yield of 85%, HPLC purity was 98%, ee=98.4%.

NIR70: $^1$H NMR (400 MHz, in CDCl$_3$, 298K, δ in ppm) δ 1.46 (9H, s), 1.53-1.58 (2H, m), 1.72-1.76 (1H, d), 1.95-1.98 (1H, m), 2.55-2.69 (3H, m), 3.60 (2H, s), 4.13 (2H, m), 6.64 (2H, d), 7.01 (2H, d). MS: 221.1 (M-C$_4$H$_8$+H). [α]$^{25}$D-72.7° (c 1.0, CHCl$_3$).

Embodiment 5

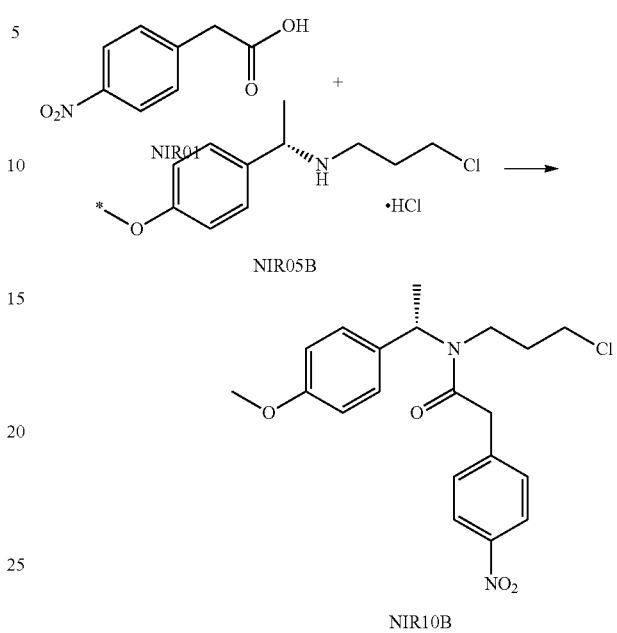

NIR05B was prepared using the method in the reference *Journal of Organic Chemistry*, 77(16), 7028-7045, 2012.

NIR05B (19 g, 84 mmol), NIR01 (18.2 g, 100 mmol), triethylamine (17 g, 168 mmol) and 200 mL dichloromethane were added into a reaction flask, followed by addition of HATU (33.5 g, 88 mmol) in portions under stirring. The reaction solution was stirred at room temperature for 18 hours. After completion of the reaction, 200 mL water was added, and the pH of the mixture was adjusted to 1 with 4N hydrochloric acid, and then extracted with 300 mL dichloromethane, washed successively with 100 mL saturated sodium bicarbonate solution and 100 mL water. The organic phase was evaporated to give a crude product, which was purified by column chromatography (petroleum ether:dichloromethane=2:1(V:V)) to give NIR10B as a red oil (29 g, yield 89%).

NIR10B: $^1$H NMR (400 MHz, in CDCl$_3$, δ in ppm) δ 1.49, 1.54 (3H, d, d); 1.75-1.89 (2H, m); 3.16-3.48 (4H, m); 3.81 (3H, s); 3.86, 3.93 (2H, s, s); 5.09, 5.98 (1H, t, t); 6.84-6.88 (2H, m); 7.05-7.24 (2H, d, d); 7.43-7.51 (2H, d, d); 8.19 (2H, d). MS: 391 (M+H).

Embodiment 6

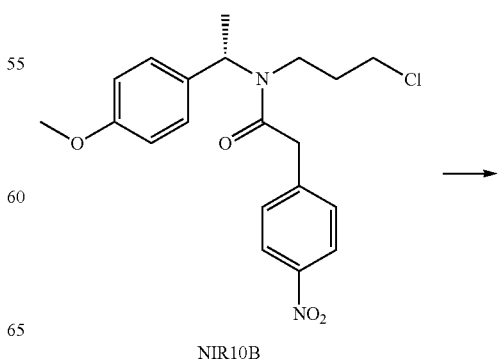

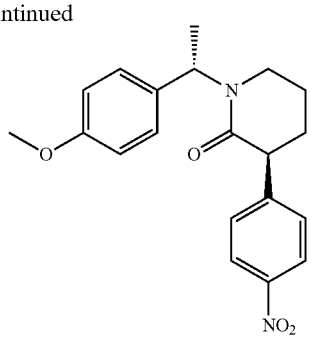

NIR30B

NIR10B (13.5 g, 34.6 mmol), anhydrous potassium carbonate (9.6 g, 69.2 mmol) and 130 mL DMF were added into a reaction flask. The reaction solution was stirred at 50° C. under nitrogen atmosphere overnight. After the reaction solution was cooled to room temperature, 500 mL water was added. The mixture was extracted twice with ethyl acetate (300 mL*2). The organic phases were combined and evaporated under reduced pressure to give a crude product of NIR30B, which was dissolved in 18 mL MTBE at 60° C. The solution was slowly cooled to room temperature under stirring, then stirred overnight and filtered. The filter cake was washed twice with 8 mL MTBE, and then dried to give pure product of NIR30B as a yellow solid (2.7 g, yield 22%). de=100% (HNMR).

NIR30B: $^1$H NMR (400 MHz, in CDCl$_3$, δ in ppm) δ 1.58 (3H, d); 1.65-1.73 (1H, m); 1.83-1.97 (2H, m); 2.12-2.21 (1H, m); 2.97 (1H, m), 3.27 (1H, m), 3.78-3.85 (1H, m), 3.80 (3H, s), 6.13 (1H, q), 6.88 (2H, d), 7.27 (2H, d), 7.38 (2H, d), 8.21 (2H, d). MS: 354.9 (M+H).

Embodiment 7

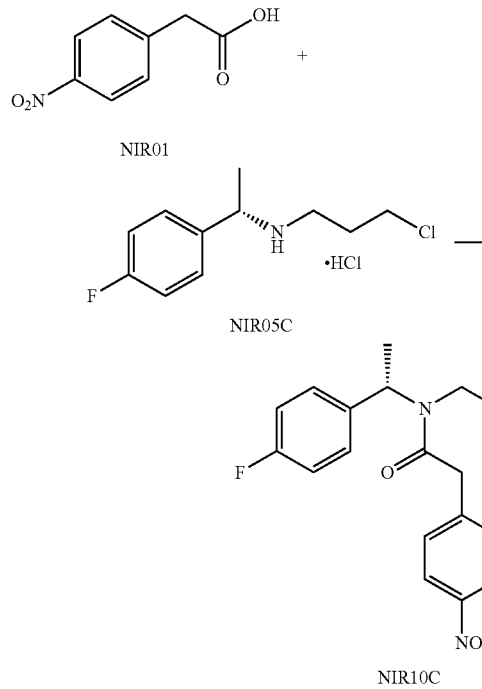

NIR05C was prepared using the method in the reference *Journal of Organic Chemistry*, 77(16), 7028-7045, 2012.

NIR05C (16 g, 74 mmol), NIR01 (14.8 g, 82 mmol), triethylamine (15 g, 148 mmol) and 170 mL dichloromethane were added into a reaction flask, followed by addition of HATU (29.5 g, 78 mml) in portions under stirring. The reaction solution was stirred at room temperature for 4 hours. After completion of the reaction, 200 mL water was added, and the pH of the mixture was adjusted to 1 with 4N hydrochloric acid, then extracted with 200 mL dichloromethane, washed successively with 150 mL saturated sodium bicarbonate solution and 150 mL water. The organic phase was evaporated under reduced pressure to give a crude product, which was purified by column chromatography (petroleum ether:dichloromethane=2:1(V:V)) to give NIR10C as a red oil (22.2 g, yield 79%).

NIR10C: $^1$H NMR (400 MHz, in CDCl$_3$, δ in ppm) δ 1.51-1.64 (3H, m); 1.82-1.93 (2H, m); 3.11-3.51 (4H, m); 3.86, 3.92 (2H, s, s); 5.12, 5.99 (1H, t, t); 7.00-7.07 (2H, m); 7.08-7.30 (2H, m, m); 7.42-7.50 (2H, m); 8.19 (2H, d). MS: 378.9 (M+H).

Embodiment 8

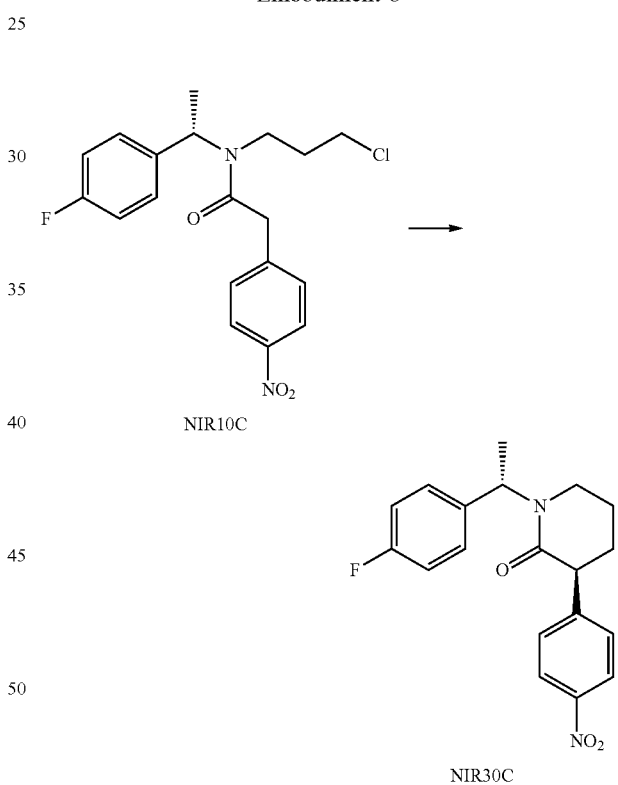

NIR10C (10 g, 26.4 mmol) and DMF (100 mL) were added into a reaction flask, followed by addition of anhydrous potassium carbonate (7.3 g, 52.8 mmol) under stirring. The reaction solution was stirred at 50° C. under nitrogen atmosphere overnight. After the reaction solution was cooled to room temperature, 300 mL of water was added, and the mixture was extracted three times with ethyl acetate (300 mL*3). The organic phases were evaporated under reduced pressure to give a crude product, which was dissolved in 15 mL MTBE at 60° C. The solution was slowly cooled to room temperature under stirring, then stirred overnight and filtered. The filter cake was washed twice with 5 mL MTBE and dried to give NIR30C as a yellow solid (2.5 g, yield 28%). de=100% (HNMR).

NIR30C: $^1$H NMR (400 MHz, in CDCl$_3$, δ in ppm) δ 1.57 (3H, d); 1.65-1.74 (1H, m); 1.85-1.97 (2H, m); 2.18 (1H, m); 2.96 (1H, m), 3.29 (1H, m), 3.81 (1H, m), 3.80 (3H, s), 6.15 (1H, q), 7.04 (2H, m), 7.31 (2H, m), 6.40 (2H, m), 8.21 (2H, d). MS: 342.9 (M+H).

Embodiment 9

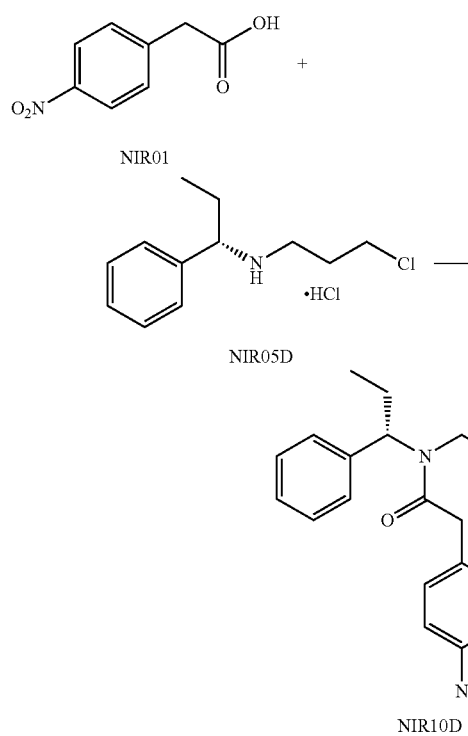

NIR5D was prepared using the method in the reference *Journal of Organic Chemistry*, 77(16), 7028-7045, 2012.

NIR05D (6.25 g, 29.5 mmol), NIR01 (5.3 g, 29.5 mmol), triethylamine (6.0 g, 59 mmol) and 60 mL of dichloromethane were added into a reaction flask, followed by addition of HATU (1.8 g, 31 mml) in portions under stirring. The reaction solution was stirred at room temperature for 16 hours. After completion of the reaction, 150 mL water was added, and the pH of the mixture was adjusted to 1 with 1N hydrochloric acid, then extracted twice with dichloromethane (150 mL*2), washed successively with 100 mL saturated sodium bicarbonate solution and 30 mL water. The organic phases were evaporated under reduced pressure to give a crude product, which was purified by column chromatography (petroleum ether:dichloromethane=3:1(V:V)) to give NIR10D as a red oil (9.5 g, yield 86%).

NIR10D: $^1$H NMR (400 MHz, in CDCl$_3$, δ in ppm) δ 0.83-1.02 (3H, m); 1.35-2.20 (4H, m); 3.15-3.43 (4H, m); 3.87, 3.99 (2H, d, s); 4.85, 5.80 (1H, t, t); 7.15-7.36 (5H, m); 7.49 (2H, m); 8.20 (2H, m). MS: 374.9 (M+H).

Embodiment 10

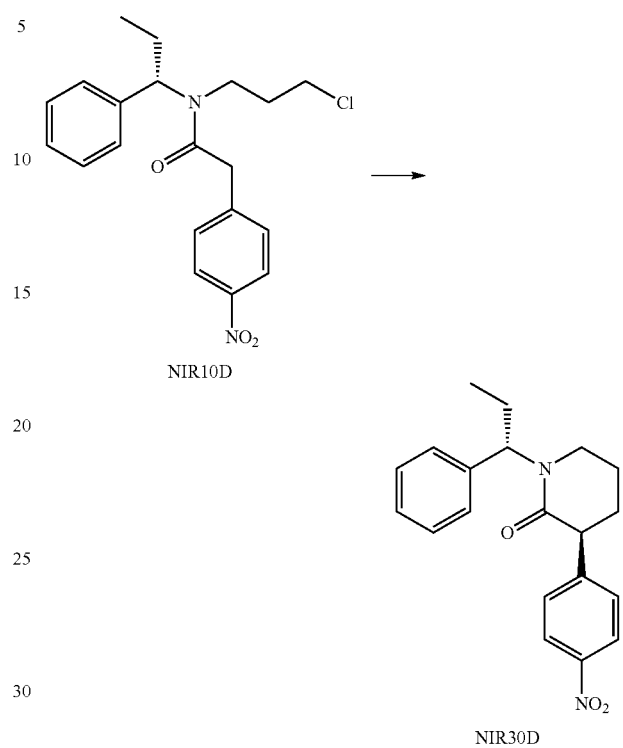

Anhydrous potassium carbonate (6.8 g, 49.6 mmol) and 30 mL DMF were added into a reaction flask, followed by dropwise addition of a solution of NIR10D (9.3 g, 24.8 mmol) in DMF (4 mL) under stirring. The reaction solution was stirred at 50° C. under nitrogen atmosphere for 6 hours. After the reaction solution was cooled to room temperature, 600 mL water was added, and then the mixture was extracted three times with ethyl acetate (100 mL*3). The organic phase was evaporated under reduced pressure to give 8.3 g crude product. 14 mL MTBE was added to the crude product, and the mixture was gradually warmed to 50° C. and the crude product was completely dissolved. The solution was naturally cooled to room temperature, then cooled under an ice bath and filtered. The filter cake was washed twice with cold MTBE and then dried to give NIR30D as a white solid (2.6 g, yield 30%). de=100% (HNMR).

NIR30D: $^1$H NMR (400 MHz, in CDCl$_3$, δ in ppm) δ 1.05 (3H, d); 1.68 (1H, m); 1.86-2.19 (5H, m); 3.01 (1H, m), 3.24 (1H, m), 3.82 (1H, m), 5.95 (1H, q), 7.27-7.38 (5H, m), 7.40 (2H, d), 8.20 (2H, d). MS: 339.0 (M+H).

Embodiment 11

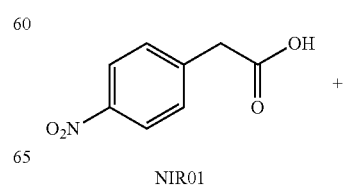

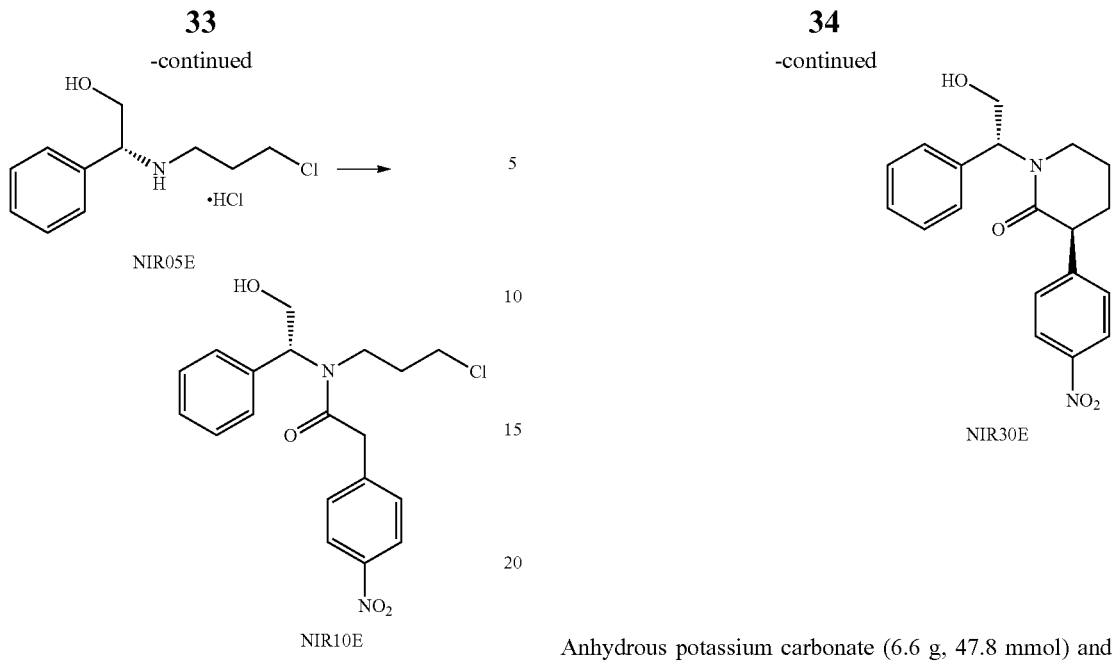

NIR05E was prepared using the method in the reference *Journal of Organic Chemistry*, 77(16), 7028-7045, 2012.

NIR05E (11.45 g, 53.7 mmol), NIR01 (12.65 g, 69.9 mmol), triethylamine (10.85 g, 56.4 mmol) and 100 mL dichloromethane were added into a reaction flask, followed by addition of HATU (21.4 g, 56.4 mmol) in portions under stirring. The reaction solution was stirred at room temperature for 16 hours. After completion of the reaction, 50 mL water was added, then the pH of the mixture was adjusted to 1 with 4N hydrochloric acid, extracted with 50 mL dichloromethane, washed successively with 70 mL saturated sodium bicarbonate solution and 50 mL water. The organic phase was evaporated under reduced pressure to give a crude product, which was purified by column chromatography (petroleum ether:ethyl acetate=4:1(V:V)) to give NIR10E as a red oil (7 g, yield 35%).

NIR10E: $^1$H NMR (400 MHz, in CDCl$_3$, δ in ppm) δ 1.66, 1.95 (2H, m, m); 3.27-3.46 (4H, m); 3.85-4.17 (4H, m); 5.14, 5.55 (1H, m, m); 7.04-7.37 (5H, m); 7.47 (2H, m); 8.19 (2H, m). MS: 377.0 (M+H).

Embodiment 12

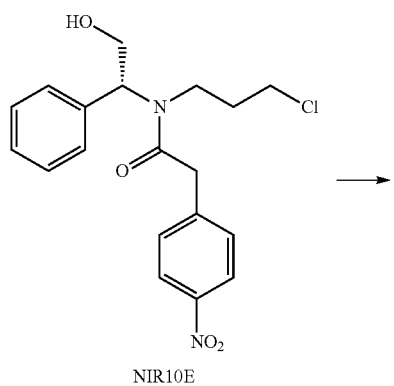

Anhydrous potassium carbonate (6.6 g, 47.8 mmol) and 50 mL DMF were added into a reaction flask, followed by dropwise addition of a solution of NIR10E (9 g, 23.9 mmol) in DMF (50 mL) under stirring. The reaction solution was stirred at 50° C. under nitrogen atmosphere for 6 hours. After the reaction solution was cooled to room temperature, 200 mL water was added, and then the mixture was extracted three times with ethyl acetate (200 mL*3). The organic phases were combined and evaporated under reduced pressure to give a crude product, which was dissolved in 14 mL MTBE under heating condition (50° C.). The solution was slowly cooled to room temperature under slowly stirring, then stirred overnight and filtered. The filter cake was washed twice with 10 mL MTBE and then dried to give NIR30E as a white solid (500 mg, yield 6%). de=100% (HNMR).

NIR30E: $^1$H NMR (400 MHz, in CDCl$_3$, δ in ppm) δ 1.76 (1H, m); 1.90 (2H, m); 2.21 (1H, m), 3.09 (1H, m), 3.37 (1H, m), 3.88 (1H, m), 4.21 (2H, m), 5.97 (1H, q), 7.28-7.40 (5H, m), 7.43 (2H, d), 8.20 (2H, d). MS: 340.9 (M+H).

It is to be understood that the foregoing description of two preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A process for preparing compound f, comprising precipitating a solid from a mixed solution formed by the mixture containing compound f and compound f1 with a solvent; the solvent is selected from the group consisting of a nitriles solvent, an esters solvent, an ethers solvent, a mixed solvent of an ethers solvent and an alkanes solvent, a mixed solvent of a nitriles solvent and an alkanes solvent, and a mixed solvent of an esters solvent and an alkanes solvent;

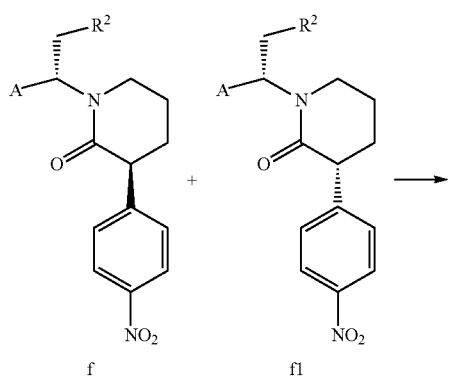

f     f1

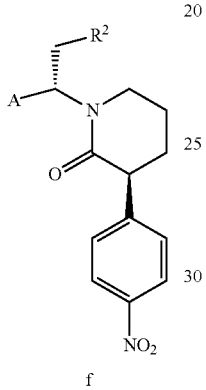

f wherein, A is an aryl or a heteroaryl, each of which is optionally substituted by the substituent(s) selected from the group consisting of H, D, an alkyl, hydroxy, an alkoxy, a halogen, an aryl, an aryloxy, an alkynyl, an alkenyl, a cycloalkyl, a cycloalkenyl, amino, an acyl, a heteroaryl, a heterocycloalkyl, an acylamido, nitro, cyano, mercapto or a haloalkyl; $R^2$ is H, an alkyl, hydroxy or an alkoxy; wherein the number of the substituent(s) is 1 to 6.

2. The process for preparing compound f as defined in claim 1, wherein, the nitriles solvent is acetonitrile;

and/or, the esters solvent is ethyl acetate;

and/or, the ethers solvent is methyl tert-butyl ether;

and/or, the alkanes solvent is a $C_5$-$C_8$ alkanes solvent;

and/or, the mixture containing compound f and compound f1 is composed of compound f and compound f1, or the amount of compound f and compound f1 determined by HPLC is 70% or more, 75% or more, 80% or more, 85% or more, 90% or more, 95% or more, or 99% or more of the mixture;

and/or, the mixture containing compound f and compound f1 is mixed with the solvent at 0° C. to the reflux temperature of the solvent under normal pressure;

and/or, the temperature for precipitating a solid is −5 to 30° C.;

and/or, the mixture containing compound f and compound f1 is mixed with the solvent under the protection of a gas;

and/or, A is

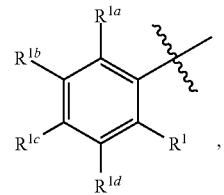

wherein, each of $R^1$, $R^{1a}$, $R^{1b}$, $R^{1c}$ and $R^{1d}$ is independently H, D, an alkyl, hydroxy, an alkoxy, a halogen, an aryl, an aryloxy, an alkynyl, an alkenyl, a cycloalkyl, a cycloalkenyl, amino, an acylamido, a heteroaryl, a heterocycloalkyl, an acylamido, nitro, cyano, mercapto or a haloalkyl;

and/or, $R^2$ is H, an alkyl, hydroxy or an alkoxy.

3. The process for preparing compound f as defined in claim 1, wherein, further comprising recrystallizing the precipitated solid;

and/or, A is

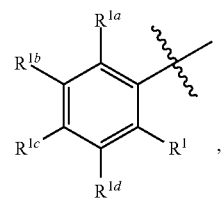

wherein, each of $R^1$, $R^{1a}$, $R^{1b}$, $R^{1c}$, and $R^{1d}$ is independently H, an alkoxy or a halogen;

and/or, $R^2$ is H, an alkyl or hydroxy.

4. The process for preparing compound f as defined in claim 1, wherein, further comprising recrystallizing the precipitated solid; the solvent for recrystallization is an ethers solvent, a nitriles solvent, an esters solvent, a mixed solvent of an ethers solvent and an alkanes solvent, a mixed solvent of a nitriles solvent and an alkanes solvent, or a mixed solvent of an esters solvent and an alkanes solvent; the recrystallization temperature is 0° C. to the reflux temperature of the solvent under normal pressure; the number of times of the recrystallization is 1 to 5 times;

and/or, A is

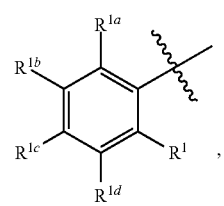

wherein, $R^1$, $R^{1a}$, $R^{1b}$, and $R^{1d}$ are H, $R^{1c}$ is H, an alkoxy or a halogen; $R^2$ is H, an alkyl or hydroxy.

5. The process for preparing compound f as defined in claim 1, wherein, the process for preparing the mixture containing compound f and compound f1 comprises conducting a cyclization reaction of compound e in a solvent and in the presence of a base to give compound f as shown below;

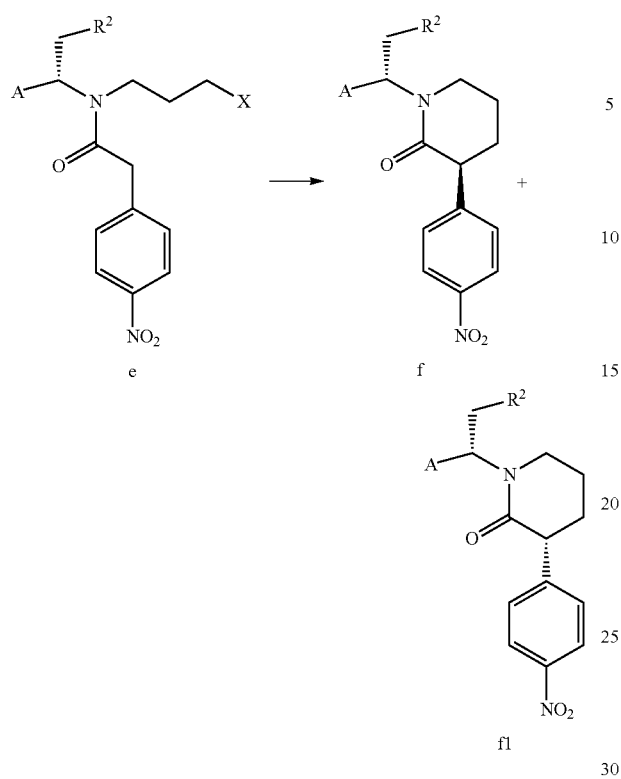

A and R² are defined as claim 1; X is a leaving group.

6. A process for preparing compound f, comprising conducting a cyclization reaction of compound e in a solvent and in the presence of a base to give compound f as shown below;

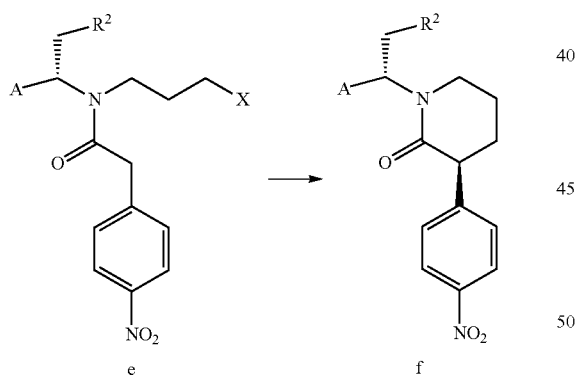

wherein, A and R² are defined as claim 1; X is a leaving group.

7. The process for preparing compound f as defined in claim 6, wherein, further comprising a recrystallization treatment after completion of the cyclization reaction; the solvent for recrystallization is an ethers solvent, a nitriles solvent, an esters solvent, a mixed solvent of an ethers solvent and an alkanes solvent, a mixed solvent of a nitriles solvent and an alkanes solvent, or a mixed solvent of an esters solvent and an alkanes solvent.

8. The process for preparing compound f as defined in claim 6, wherein, further comprising conducting an amidation reaction of compound c or an acidic salt of compound c and compound d in a solvent in the presence of a condensing agent to give compound e as shown below;

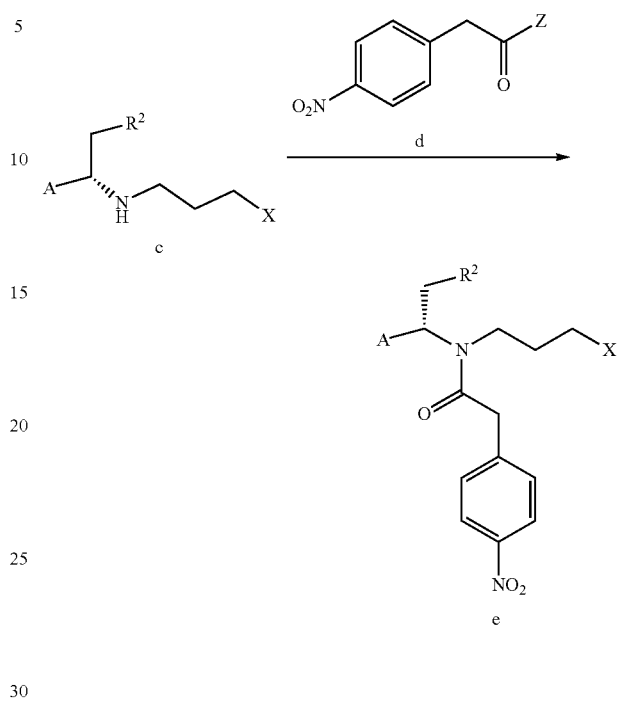

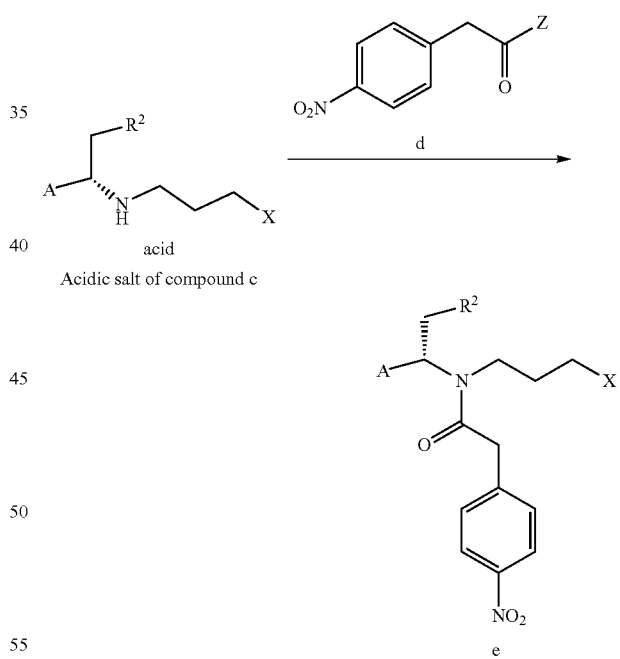

A and R² are defined as claim 1, X is a leaving group; Z is a leaving group.

9. The process for preparing compound f as defined in claim 8, wherein, in the process for preparing compound e, the solvent is a haloalkanes solvent and/or an esters solvent and/or, the condensing agent is N,N'-carbonyldiimidazole or 2-(7-azabenzotriazol-1-yl)-N,N,N',N'-tetramethyluronium hexafluorophosphate.

10. The process for preparing compound f as defined in claim 8, wherein, the process for preparing compound e comprises mixing a mixed solution of the acidic salt of compound c or compound c, compound d and the solvent, and a mixed solution of the condensing agent and the solvent at −5 to 5° C. to conduct the reaction.

11. The process for preparing compound f as defined in claim 8, wherein, further comprising conducting a substitution reaction of compound a and compound b to give compound c as shown below;

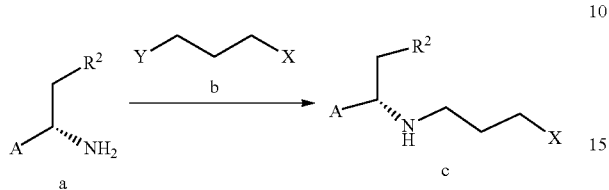

A and $R^2$ are defined as claim 1, each of X and Y is a leaving group wherein Y is easier to leave than X.

12. A compound selected from the group consisting of compound e, compound f, compound g, compound f1 and compound ff as shown below;

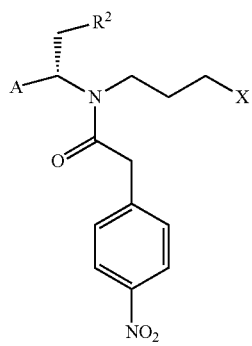

e

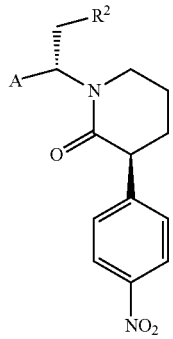

f

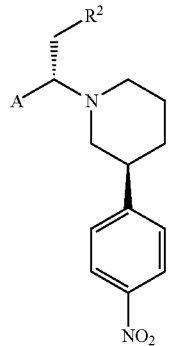

g

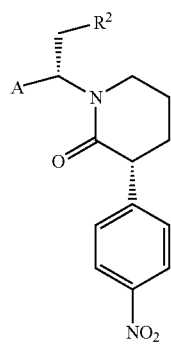

f1

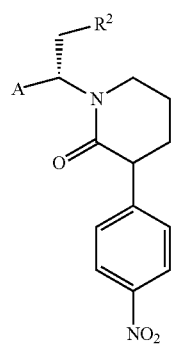

ff wherein, A and $R^2$ are defined as claim 1; X is a leaving group.

13. The compound as defined in claim 12, wherein, compound e is selected from the group consisting of

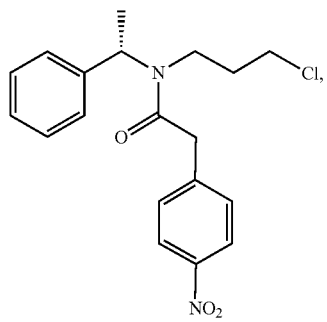

NIR10A

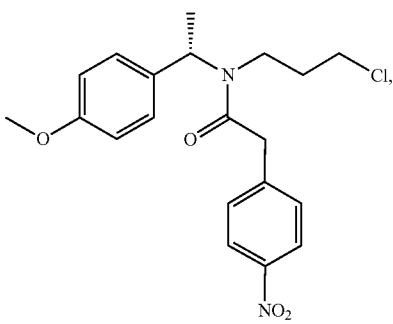

NIR10B

NIR10C
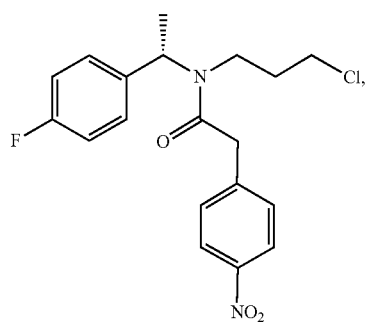
NIR10D
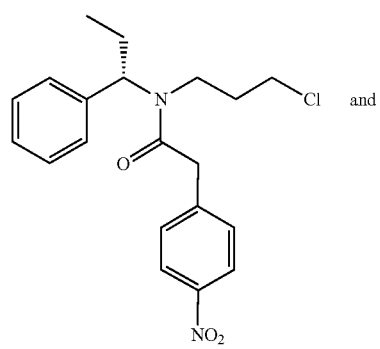
and
NIR10E
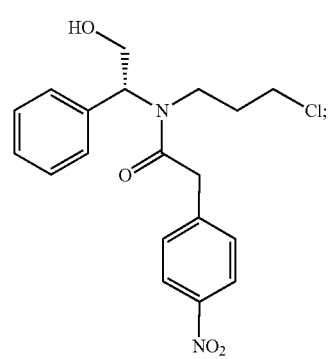
compound f is selected from the group consisting of
NIR30A
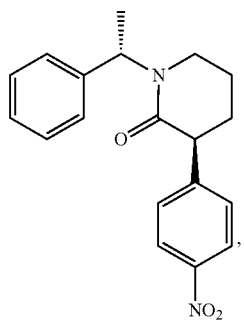
NIR30B
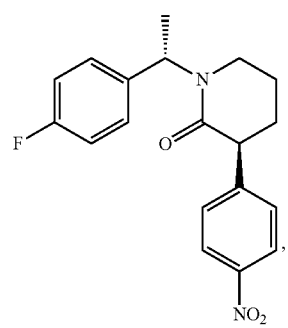
NIR30C
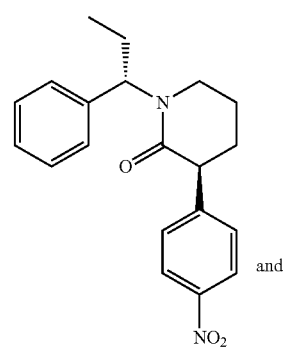
NIR30D
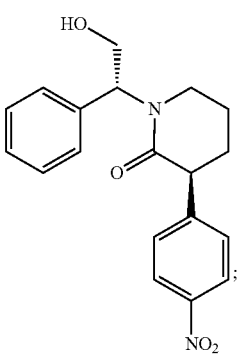
and
NIR30E compound g is

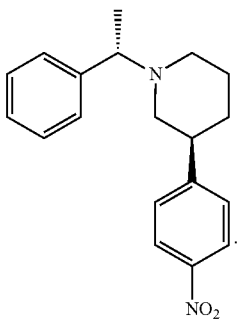

NIR40A

14. The process for preparing compound f as defined in claim 2, wherein, the mixture containing compound f and compound f1 is mixed with the solvent at 30° C. to the reflux temperature of the solvent under normal pressure;

and/or, the temperature for precipitating a solid is −5 to 5° C.

15. The process for preparing compound f as defined in claim 2, wherein, the mixture containing compound f and compound f1 is mixed with the solvent at 30 to 50° C.

16. The process for preparing compound f as defined in claim 4, wherein, the recrystallization temperature is 0 to 60° C.

17. The process for preparing compound f as defined in claim 4, wherein, the recrystallization temperature is 30 to 50° C.

18. The process for preparing compound f as defined in claim 8, wherein, X is a halogen, methanesulfonyloxy or p-toluenesulfonyloxy;

and/or, Z is hydroxy, a halogen, an alkoxy, pyrrolidin-2, 5-dione-1-oxy, isoindole-1,3-dione-2-oxy or 1H-benzotriazol-1-oxy.

19. The process for preparing compound f as defined in claim 9, the solvent is dichloromethane and/or isopropyl acetate.

20. The process for preparing compound f as defined in claim 10, wherein the mixed solution of the condensing agent and the solvent is added dropwise to the mixed solution of the acidic salt of compound c or compound c, compound d and the solvent.

* * * * *